US008518663B2

(12) United States Patent
Trevejo et al.

(10) Patent No.: US 8,518,663 B2
(45) Date of Patent: Aug. 27, 2013

(54) **RAPID DETECTION OF VOLATILE ORGANIC COMPOUNDS FOR IDENTIFICATION OF *MYCOBACTERIUM TUBERCULOSIS* IN A SAMPLE**

(75) Inventors: Jose M. Trevejo, Brighton, MA (US); Preshious Rearden, Melrose, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 339 days.

(21) Appl. No.: 12/767,928

(22) Filed: Apr. 27, 2010

(65) Prior Publication Data

US 2010/0291617 A1 Nov. 18, 2010

Related U.S. Application Data

(60) Provisional application No. 61/172,946, filed on Apr. 27, 2009.

(51) Int. Cl.
*C12Q 1/04* (2006.01)
*C12N 1/20* (2006.01)

(52) U.S. Cl.
USPC .......................................... 435/34; 435/253.1

(58) Field of Classification Search
None
See application file for complete search history.

(56) References Cited

U.S. PATENT DOCUMENTS

| | | | | |
|---|---|---|---|---|
| 4,386,157 | A | 5/1983 | Beggs et al. | |
| 4,851,338 | A | 7/1989 | Mardh et al. | |
| 5,457,316 | A | 10/1995 | Cohen et al. | |
| 5,783,410 | A | 7/1998 | He et al. | |
| 5,807,701 | A | 9/1998 | Payne et al. | |
| 5,989,824 | A | 11/1999 | Birmingham et al. | |
| 6,068,988 | A | 5/2000 | Schabert et al. | |
| 6,102,872 | A | 8/2000 | Doneen et al. | |
| 6,177,266 | B1 | 1/2001 | Krishnamurthy et al. | |
| 6,660,470 | B1 | 12/2003 | Sanders | |
| 6,897,437 | B2 | 5/2005 | Fuhrer et al. | |
| 6,996,472 | B2 | 2/2006 | Wilkes et al. | |
| 7,057,168 | B2 * | 6/2006 | Miller et al. | 250/287 |
| 7,241,989 | B2 | 7/2007 | Miller et al. | |
| 7,355,170 | B2 | 4/2008 | Miller et al. | |
| 2004/0115319 | A1 | 6/2004 | Morris et al. | |
| 2004/0185455 | A1 | 9/2004 | Shimada et al. | |
| 2005/0026813 | A1 | 2/2005 | Olstein et al. | |
| 2005/0085740 | A1 | 4/2005 | Davis et al. | |
| 2006/0163471 | A1 | 7/2006 | Zapata et al. | |
| 2006/0188868 | A1 | 8/2006 | Lloyd et al. | |
| 2006/0223052 | A1 | 10/2006 | MacDonald et al. | |
| 2006/0257955 | A1 | 11/2006 | Colpas et al. | |
| 2007/0003996 | A1 | 1/2007 | Hitt et al. | |
| 2007/0212715 | A1 | 9/2007 | Yamanaka et al. | |
| 2009/0230300 | A1 | 9/2009 | Trevejo et al. | |
| 2009/0239252 | A1 | 9/2009 | Trevejo et al. | |

FOREIGN PATENT DOCUMENTS

| | | |
|---|---|---|
| EP | 0124193 | 11/1984 |
| EP | 0158497 | 10/1985 |
| EP | 0264221 | 4/1988 |
| EP | 0482619 | 4/1992 |
| EP | 0765399 | 4/1997 |
| EP | 1726662 | 11/2006 |
| WO | WO-9404705 | 3/1994 |
| WO | WO-9429480 | 12/1994 |
| WO | WO-0157533 | 8/2001 |
| WO | WO-02073154 | 9/2002 |
| WO | WO-03063693 | 8/2003 |
| WO | WO-2005065307 | 7/2005 |
| WO | WO-2006079846 | 8/2006 |
| WO | WO-2006127974 | 11/2006 |
| WO | WO-2007003154 | 1/2007 |
| WO | WO-2007053170 | 5/2007 |
| WO | WO-2008030113 | 3/2008 |
| WO | WO-2009037492 | 3/2009 |
| WO | WO-2009045116 | 4/2009 |
| WO | WO-2009091375 | 7/2009 |

OTHER PUBLICATIONS

Pandey et al. "Mycobacterial resistance requires the utilization of host cholesterol". PNAS. Mar. 2008, vol. 105, No. 11, pp. 4376-4380.*

Salvi et al. Journal of Bacteriology, Jun. 2008, vol. 190, No. 11, pp. 3886-3895.*

Allardyce et al., (2006) "Detection of volatile metabolites produced by bacterial growth in blood culture media by selected ion flow tube mass spectrometry (SIFT-MS)," Journal of Microbiological Methods, vol. 65(2), pp. 361-365.

Allardyce, R., et al., (2006) "The rapid evaluation of bacterial growth and antibiotic susceptibility in blood cultures by selected ion flow tube mass spectrometry," Diagnostic Microbiology and Infectious Diseases, vol. 55, pp. 255-261.

Bunge, M., et al., (2008) "On-line monitoring of microbial volatile metabolites by proton transfer reaction-mass spectrometry," Appl Environ Microbiol., vol. 74(7), pp. 2179-2186 (Abstract only).

Camargo, E., et al., (1982) "Radiometric Measurement of Differential Metabolism of Fatty-Acid by Mycobacteria" International Journal of Leprosy and Other Mycobacterial Diseases, vol. 50(2), pp. 200-204.

Claeson, A., et al., (2002) "Volatile metabolites from microorganisms grown on humid building materials and synthetic media," J Environment Monit., vol. 4(5), pp. 667-672 (Abstract only).

Deng, C., et al., (2004) "Determination of acetone in human breath by gas chromatography-mass spectrometry and solid-phase microextraction with on-fiber derivatization," Journal of Chromatography B, vol. 810, pp. 269-275.

Elgaali, H., et al., (2002) "Comparison of long-chain alcohols and other volatile compounds emitted from food-borne and related Gram positive and Gram negative bacteria," J Basic Microbiol., vol. 42(6), pp. 373-380 (Abstract only).

(Continued)

*Primary Examiner* — Vera Afremova

(74) *Attorney, Agent, or Firm* — Foley & Lardner LLP; Edward A. Gordon

(57) ABSTRACT

In various embodiments, the invention relates to a method for identifying the presence of particular bacteria in a sample. The method includes collecting a sample that includes or has been exposed to the particular bacteria and detecting, in the sample, at least one volatile organic compound indicative of the presence of the bacteria.

21 Claims, 19 Drawing Sheets

(56) References Cited

OTHER PUBLICATIONS

Fend, R., et al., (2006) "Prospects for Clinical Application of Electronic-Nose Technology to Early Detection of *Mycobacterium tuberculosis* in Culture and Sputum," Journal of Clinical Microbiology, vol. 44(6), pp. 2039-2045.

Garner, C., et al., (2007) "Volatile organic compounds from feces and their potential for diagnosis of gastrointestinal disease," FASEB Journal, vol. 21, pp. 1675-1688.

Giardina, M., et al., (2003) "Application of low-temperature glassy carbon-coated macrofibers for solid-phase microextraction analysis of simulated breath volatiles," Anal Chem, vol. 75(7), pp. 1604-1614 (Abstract only).

Hakoköngäs, L., et al., (2004) "Running out of breath? TB care in the 21st Century," Medecins Sans Frontieres, pp. 1-32.

Jackman, J., et al., (2004) "Mass Spectrometry of Breath for the Diagnosis of Infection and Exposure," Johns Hopkins APL Technical Digest, vol. 25(1), pp. 6-13.

Krebs, M., et al., (2006) "Novel technology for rapid species-specific detection of *Bacillus* spores," Biomolecular Engineering, vol. 23, pp. 119-127.

Labows, J., et al., (1980) "Headspace Analysis of Volatile Metabolites of *Pseudomonas aeruginosa* and Related Species by Gas Chromatography-Mass Spectrometry," Journal of Clinical Microbiology, vol. 12(4), pp. 521-526.

Lechner, M., et al., (2005) "Diagnosis of bacteria in vitro by mass spectrometric fingerprinting: a pilot study," Curr Microbiol., vol. 51(4), pp. 267-269 (Abstract only).

Miekisch, W., et al., (2004) "Diagnostic potential of breath analysis-focus on volatile organic compounds," Clinica Chimica Acta, vol. 347, pp. 25-39.

Pavlou, A., et al., (2004) "Detection of *Mycobacterium tuberculosis* (TB) in vitro and in situ using an electronic nose in combination with a neural network system," Biosensors & Bioelectronics, vol. 20, pp. 538-544.

Perkins, M., (2000) "New diagnostic tools for tuberculosis," Int J Tuberc Lung Dis, vol. 4(12), S182-S188.

Phillips, M., et al., (2007) "Volatile Biomarkers of pulmonary tuberculosis in the breath" Tuberculosis, vol. 87, pp. 44-52.

Ruiz, J., et al., (2001) "New Device for Direct Extraction of Volatiles in Solid Samples Using SPME," Journal of Agricultural and Food Chemistry, vol. 49(11), pp. 5115-5121.

Schmidt, H., et al., (2004) "Microfabricated Differential Mobility Spectrometry with Pyrolysis Gas Chromatography for Chemical Characterization of Bacteria," Analytical Chemistry, vol. 76(17), pp. 5208-5217.

Senecal, A., et al., (2002) "Rapid detection of pathogenic bacteria by volatile organic compound (VOC) analysis (Proceedings Paper)," Chemical and Biological Early Warning Monitoring for Water, Food, and Ground, vol. 4575, pp. 121-131 (Abstract only).

Shnayderman, M., et al., (2005) "Species-Specific Bacteria Identification Using Differential Mobility Spectrometry and Bioinformatics Pattern Recognition," Analytical Chemistry, vol. 77(18), pp. 5930-5937.

Strachan, N.J.C., et al., (1995) "An automated sampling system using ion mobility spectrometry for the rapid detection of bacteria," Analytica Chimica Acta, vol. 313, pp. 63-67.

Syhre, M., et al., (2008) "The scent of *Mycobacterium tuberculosis*," Tuberculosis, vol. 88, pp. 317-323.

Syhre, M., et al., (2007) "Investigation into the production of 2-Pentylfuran by *Aspergillus fumigatus* and other respiratory pathogens in vitro and human breath samples," Medical Mycology, pp. 1-7.

Wheatley, R., (2002) "The consequences of volatile organic compound mediated bacterial and fungal interactions," Antonie Van Leeuwenhoek, vol. 81(1-4), pp. 357-364 (Abstract only).

Zechman, J., et al., (1985) "Volatiles of *Pseudomonas aeruginosa* and related species by automated headspace concentration—gas chromatography," Can J Microbiol., vol. 31(3), pp. 232-237 (Abstract only).

Zechman, J., et al., (1986) "Characterization of pathogenic bacteria by automated headspace concentration-gas chromatorgraphy," J Chromatogr., vol. 377, pp. 49-57 (Abstract only).

Gagneux et al., "Global phylogeography of *Mycobacterium tuberculosis* and implications for tuberculosis product development", in Lancet Infect. Dis. (2007) vol. 7, pp. 328-337.

Michael Philips et al., "Volatile biomarkers of pulmonary tuberculosis in the breath", Tuberculosis vol. 87 No. I. Dapes 44-52 Jan. 31, 2007.

* cited by examiner

RAPID DETECTION OF VOLATILE ORGANIC COMPOUNDS FOR IDENTIFICATION OF *MYCOBACTERIUM TUBERCULOSIS* IN A SAMPLE

CROSS-REFERENCE TO RELATED APPLICATIONS

This application claims the benefit of and priority to U.S. Provisional Patent Application Ser. No. 61/172,946, filed Apr. 27, 2009, the contents of which are hereby incorporated by reference for all purposes.

TECHNICAL FIELD

In various embodiments, the invention relates to methods for detecting one or more volatile organic compounds (herein also referred to as "VOCs" or "organic compounds") in a sample to determine the presence or absence of one or more bacteria in the sample.

BACKGROUND

The incidence of bacterial infections, bacterial contaminations, and the spread of drug-resistant bacteria represent growing worldwide health problems. For example, over 8.8 million new cases of tuberculosis are estimated to occur worldwide per year. Recent news has also highlighted the emergence of resistant strains of tuberculosis, which pose a danger to travelers using mass transit, such as commercial airplanes. Rapid detection of the presence or absence of bacteria, of the quantity or bacterial load of bacteria, and of resistant strains of bacteria, such as tuberculosis, is a top priority of health organizations such as the World Health Organization.

Current methods of detecting the presence or absence of bacteria typically include culturing a sample suspected of having bacteria followed by isolation and use of various biochemical tests. These tests may take between 2-21 days to complete depending on how long it takes to isolate and grow the bacteria. Accordingly, while such biochemical testing is relatively inexpensive, it is time consuming to grow and subculture bacteria in a sample to reach the minimal concentration of bacteria needed for testing.

There are PCR-based methods for rapidly detecting bacteria, but these typically are expensive and require advanced laboratory equipment and techniques and various reagents for use. Furthermore, there typically is frequent contamination of samples that precludes use in more resource-limited settings. Nucleic acid amplification (NAA) systems have been used in industrialized countries for some time, and two systems have been approved by the FDA for MTb detection in sputum. NAA is more sensitive than a smear microscopy test, but less sensitive than culture. NAA, though better than smear microscopy, is expensive and typically requires considerable technical support and quality control. For example, rapid sequencing of bacteria for diagnosis and drug resistance determination (i.e. using PCR) is difficult to make portable and robust for field use. It typically requires significant power and reagents that require special treatment (i.e., cold storage). In addition, even in strictly maintained laboratories there still may be contamination leading to false positive tests. These downfalls make it an unlikely target for a system to be used in high-need (developing) countries.

By way of example, *Mycobacterium tuberculosis* (herein also referred to as "TB," "MTb," or "*M. tuberculosis*") diagnostic standards have not changed significantly in the past century. To the extent that new MTb diagnostics have been developed, they typically are not practical for wide-scale use, for example, in third-world countries. One standard for the diagnosis of active pulmonary tuberculosis is sputum smear microscopy for acid-fast bacilli. If a patient's sputum tests positive for MTb (considered "smear-positive"), they have active pulmonary tuberculosis, are considered highly infectious, and are placed on an exhaustive drug regimen for treatment. However, sputum smear microscopy has low sensitivity and typically requires appropriately trained personnel to accomplish. In fact, it is estimated that sputum smear microscopy at best detects 25-60% of people with active pulmonary tuberculosis. The method also has relatively poor limits of detection as it requires the presence of at least 10,000 MTb bacilli/mL.

Serologic tests exist for MTb diagnostics, but they continue to undergo development and tend to be more specific for exposure than active disease. Some commercialized tests use immunodominant antigens to detect immunoglobulin classes (like IgG) in an ELISA or dipstick format. Serological tests are estimated to detect one-third to three-quarters of sputum smear-positive cases of MTb. They detect a significantly smaller portion of smear-negative cases with HIV co-infection. In fact, for people infected with both HIV and MTb, serological tests detect less than one third of patients with the active form of the disease.

Phage systems that detect live mycobacteria in liquid cultures using phages that act as indicators by infecting and replicating in MTb cells have been developed. Phage systems appear to be fast, robust and highly sensitive, but little is known about their reproducibility and performance. Phage systems, though highly promising for their speed, robustness, and high sensitivity, typically require, in use, the presence of skilled professionals and may turn out to be very costly. Furthermore, phage systems appear to be inhibited by a factor in sputum, thus rendering them less useful because sputum is the sample frequently used for diagnosis. Accordingly, the systems may not lend themselves well to widespread use in developing countries.

Radiometric and fluorescent liquid culture systems, often used in level III laboratories, are highly sensitive, but also may require support of a full microbiology laboratory, typically require relatively long times (1-3 weeks) to generate results, and are relatively expensive to purchase. Radiometric liquid culture systems, though robust and sensitive, require radioactive materials, which therefore typically require special facilities and training for their use. The cost of materials also may be very high and the systems not portable.

Some non-standardized culture systems have been developed that employ inexpensive reagents and are more suitable for widespread use, but more studies are needed to determine the accuracy of these systems. At the very least, they have demonstrated performance levels comparable to standard diagnostics methods. These non-commercial liquid culture growth detection methods that employ inexpensive reagents may be more suitable for use in developing countries, but they are not yet standardized and thus have not been readily endorsed by TB diagnostics experts. They may benefit from standardization of reagents, packaging, and product support.

Another common MTb test is the tuberculin or purified protein derivative (PPD) (PPD skin test), which is the skin test developed for the screening of latent MTb. Additional screens for latent MTb now include new in vitro assays that measure IFN-γ produced by T lymphocytes in whole blood after stimulation from PPDs obtained from MTb, *M. avium* and *M. bovis*. Single specific antigens have been used to increase specificity as well. The tuberculin or PPD skin test shares many antigens with a common tuberculosis vaccine, *Bacillus* Calmette-Guerin ("BCG"), and environmental bacteria so people without latent MTb infection frequently test positive. This approach is further complicated by the need for a clinician to interpret the results and for multiple visits to a clinic by the patient to obtain the results. The skin test frequently has unreliable results in many patients including those having received a MTb vaccination or those infected with another type of mycobacteria. HIV/AIDS patients frequently test negative when they are also carriers of MTb. Additional skin tests in development (like the one that measures IFN-γ) are more specific, though not perfect, and increasing the specificity of these tests is often at the cost of sensitivity. These tests are also not useful for detecting active MTb infection, but primarily show exposure or latent MTb infection Accordingly, rapid point-of-care bacterial detection devices, methods and systems are needed, for example, to screen patients suspected of one or more bacterial infections. Preferably, such devices, methods and systems can be used in the field, for example, for onsite rapid monitoring of the bacterial infections of humans or animals (e.g., in developing countries or any location removed from a laboratory setting).

SUMMARY OF THE INVENTION

In various embodiments, the present invention addresses the limitations of current bacterial diagnosis and identification methods by utilizing sensitive detection of certain VOCs to identify the presence of certain bacteria in a sample. This allows, for example, diagnosis of bacterial infection, determination of drug efficacy, and/or diagnosis of drug-resistant bacterial strains in settings outside the laboratory. The bacteria may include, for example, *Mycobacterium tuberculosis*. Without being bound by theory, certain VOCs are believed to be associated with bacterial metabolism, and therefore may be used to detect viable, recently viable, or growing bacteria isolated in culture or present among a plurality of types of bacteria.

Accordingly, in various embodiments, the present invention is directed to detecting one or more VOCs that are associated with the metabolism, presence, and/or growth of a particular bacteria in order to detect the presence or absence, concentration, state (e.g. viable, growing, etc.) and/or drug resistance status of the bacteria and/or related bacterial strains in a sample. The one or more VOCs may be detected using a portable device, for example a point-of-care device, such as but not limited to a Differential Mobility Spectrometer ("DMS"). The one or more VOCs may be detected directly from a source, for example the exhaled breath of a human or animal (e.g., a human or animal suspected of having pulmonary tuberculosis (reactivation or primary)). The VOCs may be generated from a solid or liquid sample, for example from a bodily source, such as urine, sweat, blood, sputum, gastric lavage, and/or condensate.

In one aspect, the invention is directed to a method for identifying the presence or absence of *Mycobacterium tuberculosis* in a sample. Embodiments of the method include collecting a sample suspected of having *Mycobacterium tuberculosis* and detecting the presence or absence of one or more volatile organic compounds indicative of the presence or absence of *Mycobacterium tuberculosis* in the sample. The organic compound is or includes ethyl propionate (CAS: 105-37-3), 1-pentanol (CAS: 71-41-0), methyl valerate (CAS: 624-24-8), 1-hexanol (CAS: 111-27-3), ethyl valerate (CAS: 539-82-2), methyl caproate (CAS: 106-70-7), ethyl caproate (CAS: 123-66-0) and/or any of the foregoing compounds in isotopically labeled form. In certain other embodiments, the method further comprises detecting the presence or absence of one or more volatile organic compounds selected from the group consisting of methoxybenzene (anisole) (CAS: 100-66-3), 2-butanone (CAS: 513-86-0), methyl 2-ethylhexanoate (for example, a chiral version of methyl 2-ethylhexanoate (CAS: 816-19-3), methyl propionate (CAS: 554-12-1), 2-pentanone, 3-pentanone (CAS: 96-22-0), 2,4-dimethyl-1-heptene, methyl isobutyl ketone, 6-methyl-5-hepten-2-one, dimethylsulfoxide, dimethylsulfide, methyl 2-methylpropionate (CAS: 547-63-7), 1-ethoxy-2-methylpropane (CAS: 627-02-1), 1-ethoxy-butane (CAS: 628-81-9), t-butyl ethyl ether (CAS: 637-92-3), methyl 2-methyl butanoate (868-57-5), isobutanol (CAS: 78-83-1), the aromatic compound represented by the mass spectrum in FIG. 3, and/or any of the foregoing compounds in isotopically labeled form.

In any of these aspects, the concentration of one or more of the volatile organic compounds can be detected. The presence or concentration of the detected organic compound(s) in the sample may indicate the presence, concentration, state (e.g. viable, growing, etc.) and/or a phenotypic characteristic (e.g. antibiotic resistance, strain, etc.) of the particular bacteria. In certain embodiments, at least a portion of the one or more organic compounds is unique to a bacteria in the sample (e.g., the bacteria being detected). In certain embodiments, the organic compound(s) are detected in the gas phase. The sample itself may be in the gas phase, for example exhaled breath from an individual, or the gas may be mixed with or generated from a solid or liquid sample, such as a sample grown in culture or medium.

The sample can be obtained from any source, for example from the exhaled breath from an individual. The breath may include body fluid from the individual. Alternatively, the sample can include a fluid, for example body fluid associated with an individual's breath, sputum, blood, urine, gastric lavage or pleural fluid. In certain embodiments, the sample includes solid matter, for example tissue or fecal matter.

The sample can include bacteria exposed to a candidate therapy for treating the bacteria, for example to detect a therapy-resistant strain of the bacteria. The candidate therapy may be a candidate drug, for example an antibiotic, and the therapy-resistant strain of bacteria may be resistant to the drug. The sample can be analyzed immediately for volatile organic compounds. Alternatively, the sample can be cultured and the headspace of the cultured sample can be analyzed for volatile organic compounds (VOCs). In certain embodiments, to facilitate detection of VOCs from the headspace, the VOCs can be extracted from the headspace using a solid phase microextraction (SPME) fiber or a thermal desorption tube, or the VOCs can be introduced directly to a sensor. The detected volatile organic compounds indicative of a bacteria can be the same compounds regardless of culture conditions (e.g., media content), or the compounds can be specific to a bacteria grown in a particular culture condition. In various embodiments, the invention is directed to a method for identifying a bacteria (e.g., *Mycobacterium tuberculosis*) in a sample. The method includes collecting a sample suspected of comprising the bacteria, culturing the sample using a particular media (e.g. a media that includes propionate), and detecting one or more volatile organic compounds associated with the bacterial metabolism on the particular media that is indicative of a presence of or response to treatment or resistance of the bacteria in the cultured sample.

In various embodiments, the invention is directed to a device for identifying a certain bacteria in a sample. The device can include an input for receiving a sample suspected of certain bacteria and a means for detecting one or more volatile organic compounds indicative of a presence of or response to treatment or resistance of the bacteria in the sample. In one aspect, the device identifies *Mycobacterium tuberculosis* in the sample and the one or more volatile organic includes ethyl propionate (CAS: 105-37-3), 1-pentanol (CAS: 71-41-0), methyl valerate (CAS: 624-24-8), 1-hexanol (CAS: 111-27-3), ethyl valerate (CAS: 539-82-2), methyl caproate (CAS: 106-70-7), ethyl caproate (CAS: 123-66-0), and/or any of the foregoing compounds in isotopically labeled form. In certain other embodiments, the device further comprises means for detecting one or more of methoxybenzene (anisole) (CAS: 100-66-3), 2-butanone (CAS: 513-86-0), methyl 2-ethylhexanoate (for example, a chiral version of methyl 2-ethylhexanoate (CAS: 816-19-3), methyl propionate (CAS: 554-12-1), 2-pentanone, 3-pentanone (CAS: 96-22-0), 2,4-dimethyl-1-heptene, methyl isobutyl ketone, 6-methyl-5-hepten-2-one, dimethylsulfoxide, dimethylsulfide, methyl 2-methylpropionate (CAS: 547-63-7), 1-ethoxy-2-methylpropane (CAS: 627-02-1), 1-ethoxy-butane (CAS: 628-81-9), t-butyl ethyl ether (CAS: 637-92-3), methyl 2-methyl butanoate (868-57-5), isobutanol (CAS: 78-83-1), the aromatic compound represented by the mass spectrum in FIG. 3, and/or any of the foregoing compounds in isotopically labeled form. Alternatively or in addition, the absence of one or more of such organic compounds can be indicative of the absence or response to treatment or resistance of the corresponding bacteria in the sample.

In certain embodiments, a presence or amount of the bacteria in a sample is identified based on the presence and/or concentration of one organic compound detected in the sample. In certain embodiments, a presence or amount of a bacteria in a sample is determined based on the presence or concentration of two or more organic compounds detected in the sample. In certain embodiments, the presence and/or amount of the bacteria in a sample is identified at various time points, for example following administration of a therapy, so that a change in bacterial burden and/or efficacy of the therapy may be identified.

It is to be understood that the features of the various embodiments described herein are not mutually exclusive and may exist in various combinations and permutations.

BRIEF DESCRIPTION OF THE DRAWINGS

The foregoing and other objects, aspects, features, and advantages of embodiments of the invention will become more apparent and may be better understood by referring to the following description, taken in conjunction with the accompanying drawings, in which:

(FIG. 16 Top shows plots of DMS data obtained from a sample from the headspace of cultures (i.e., cultures containing frozen sputum, fresh sputum, or just media) that were not spiked with Mtb. FIG. 16 Bottom shows plots of DMS data obtained from a sample from the headspace of cultures (i.e., cultures containing frozen sputum, fresh sputum, or just media) that were spiked with Mtb.);

DETAILED DESCRIPTION

In various embodiments, the present invention relates to an improved method for identifying bacteria in a sample, and allows for a rapid and accurate diagnosis of certain bacterial infections or contaminations. In addition, embodiments of the invention allow for the determination of efficacy of a drug such as an antibiotic, and/or the diagnosis of certain drug-resistant bacterial strains.

Figure 3:
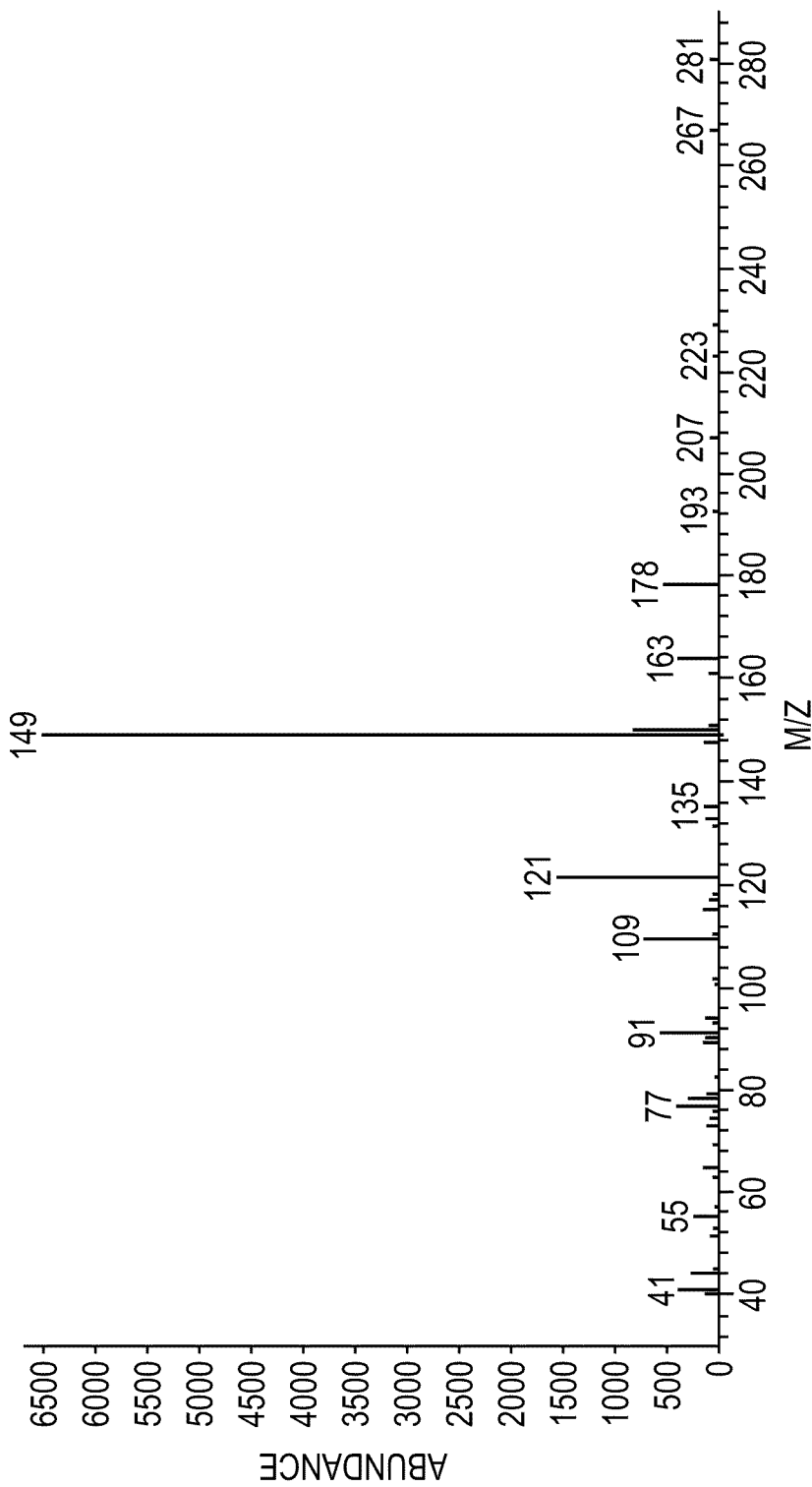
FIG. 3 depicts an exemplary mass spectrometry spectral pattern for a volatile aromatic compound previously detected in MTb cultures regardless of the lipid component in the media.
Figure 4A:
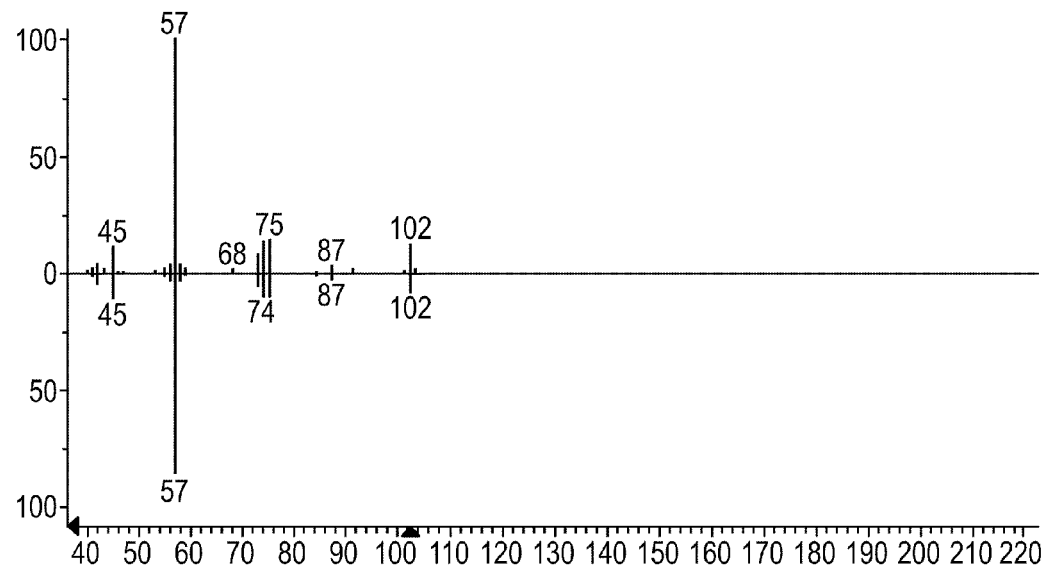
FIG. 4A depicts a mass spectrometry fragmentation pattern (top) for the compound isolated from the headspace and identified as ethyl propionate, and the National Institute of Standards and Technology mass spectrometry fragmentation pattern (bottom) for ethyl propionate.
Figure 4B:
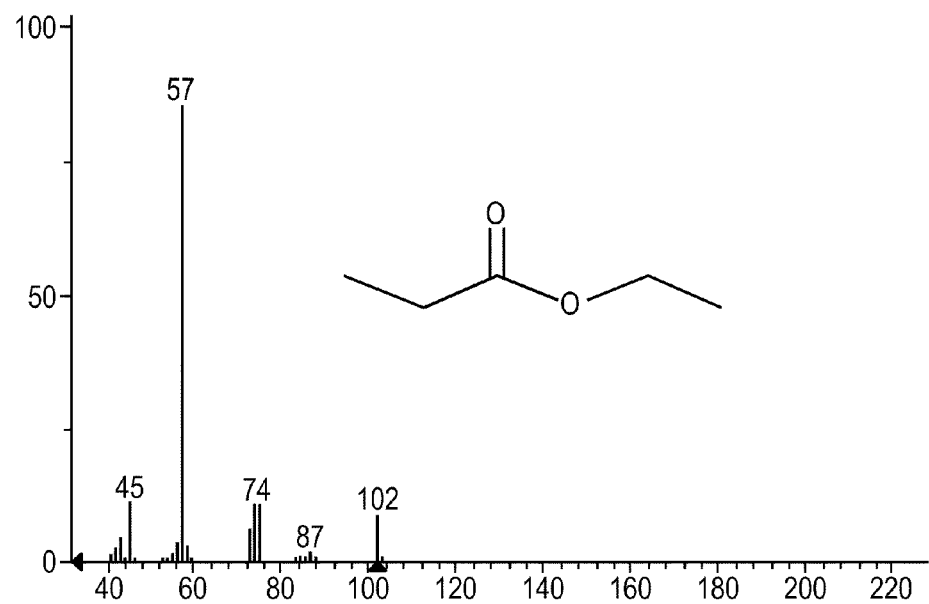
FIG. 4B depicts a mass spectrometry fragmentation pattern obtained from a purified, known sample of ethyl propionate using the GC-MS apparatus described in Example 1.
Figure 5A:
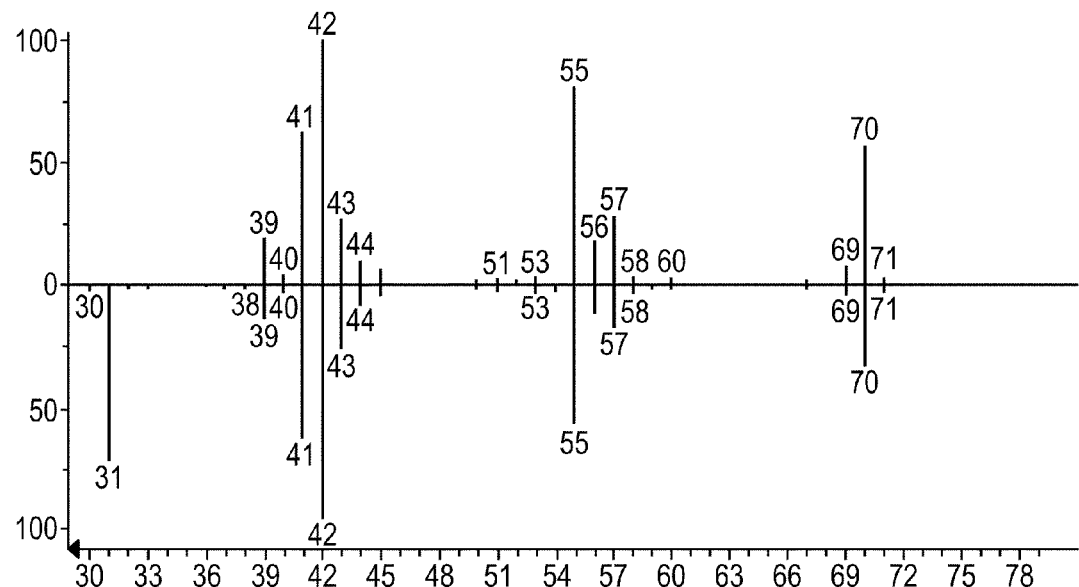
FIG. 5A depicts a mass spectrometry fragmentation pattern (top) for the compound isolated from the headspace and identified as 1-pentanol, and the National Institute of Standards and Technology mass spectrometry fragmentation pattern (bottom) for 1-pentanol.
Figure 5B:
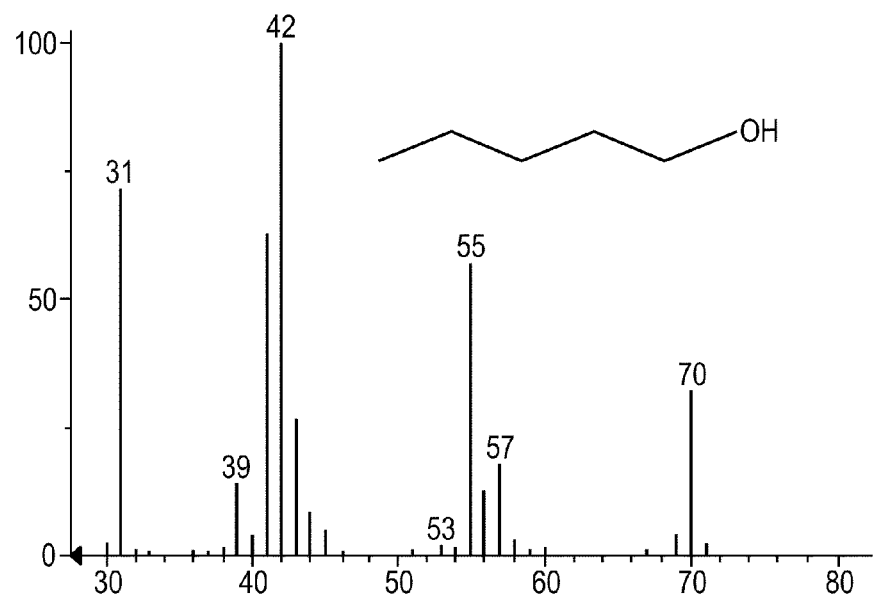
FIG. 5B depicts a mass spectrometry fragmentation pattern obtained from a purified, known sample of 1-pentanol using the GC-MS apparatus described in Example 1.
Figure 6A:
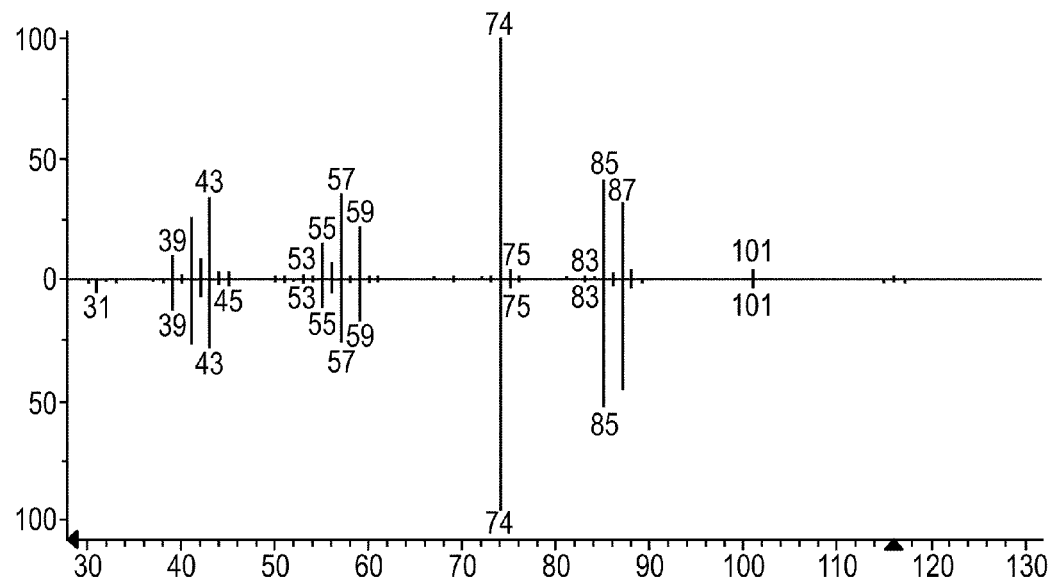
FIG. 6A depicts a mass spectrometry fragmentation pattern (top) for the compound isolated from the headspace and identified as methyl valerate, and the National Institute of Standards and Technology mass spectrometry fragmentation pattern (bottom) for methyl valerate.
Figure 6B:
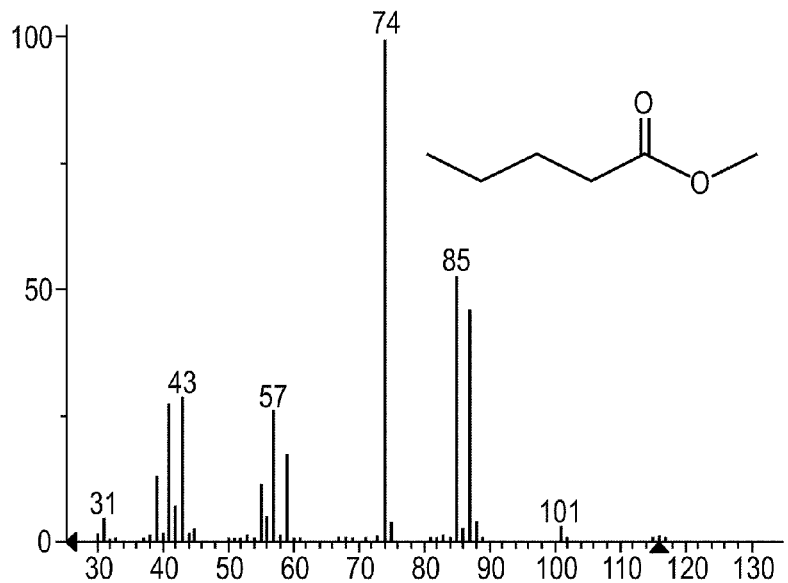
FIG. 6B depicts a mass spectrometry fragmentation pattern obtained from a purified, known sample of methyl valerate using the GC-MS apparatus described in Example 1.
Figure 7A:
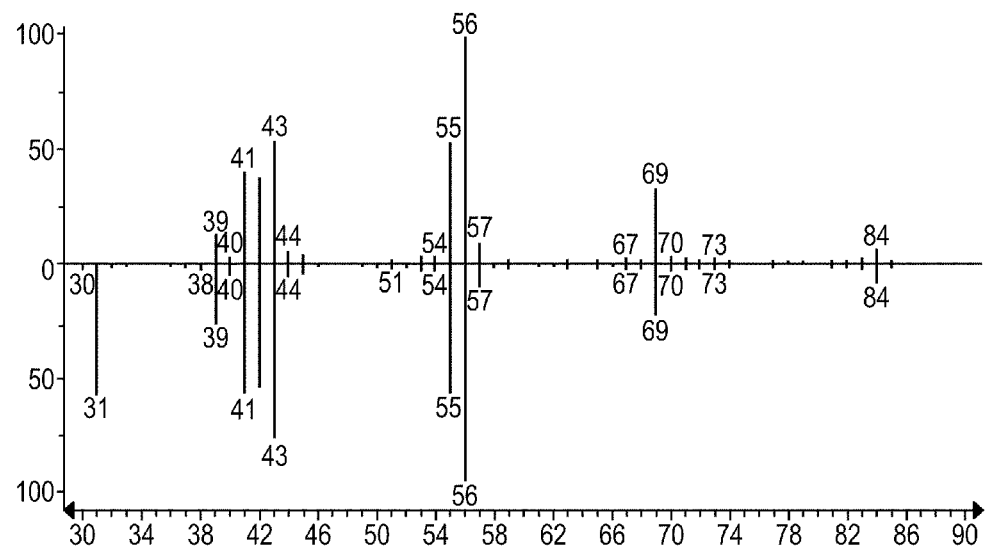
FIG. 7A depicts a mass spectrometry fragmentation pattern (top) for the compound isolated from the headspace and identified as 1-hexanol, and the National Institute of Standards and Technology mass spectrometry fragmentation pattern (bottom) for 1-hexanol.
Figure 7B:
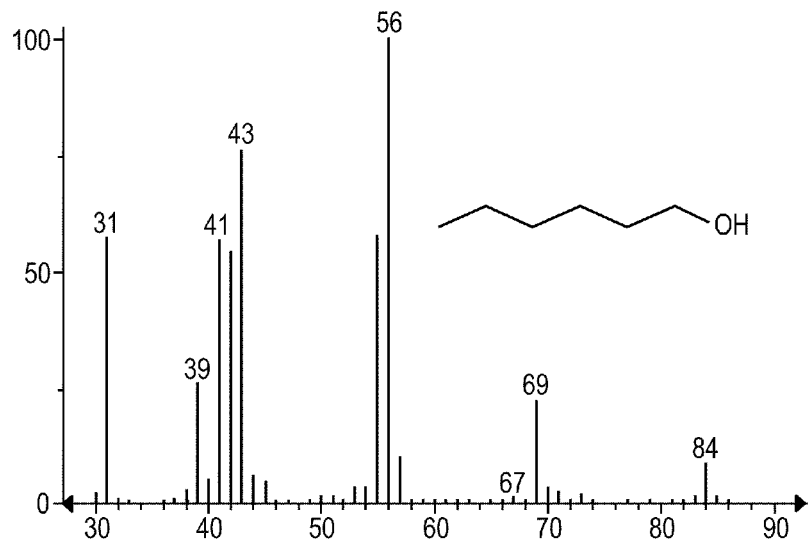
FIG. 7B depicts a mass spectrometry fragmentation pattern obtained from a purified, known sample of 1-hexanol using the GC-MS apparatus described in Example 1.
Figure 8A:
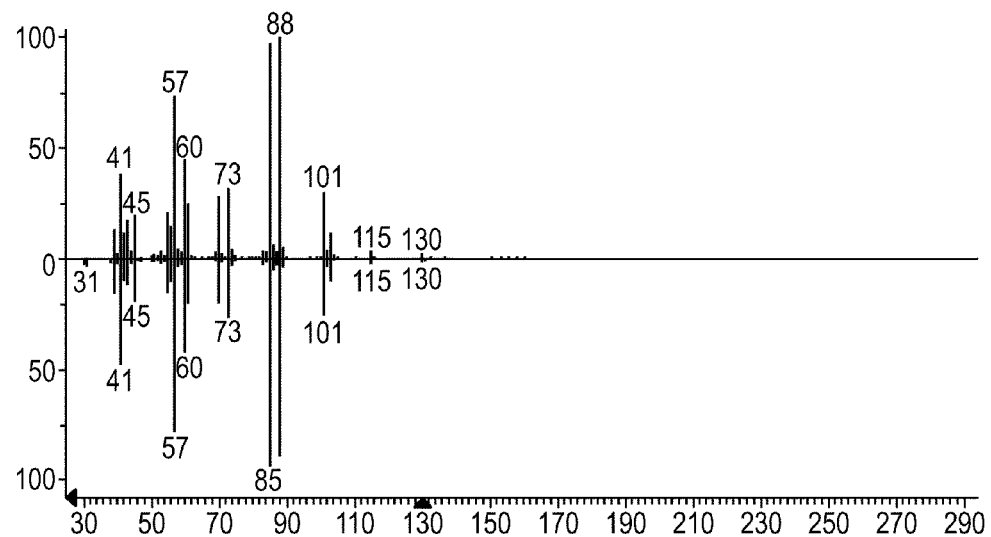
FIG. 8A depicts a mass spectrometry fragmentation pattern (top) for the compound isolated from the headspace and identified as ethyl valerate, and the National Institute of Standards and Technology mass spectrometry fragmentation pattern (bottom) for ethyl valerate.
Figure 8B:
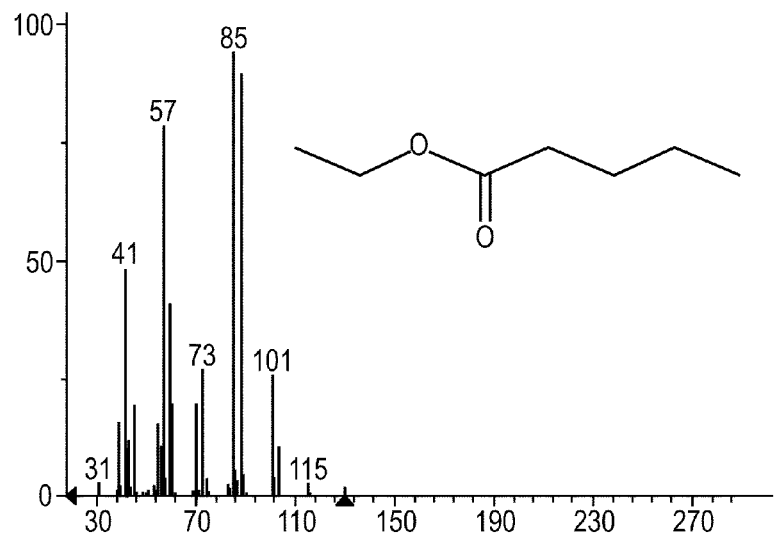
FIG. 8B depicts a mass spectrometry fragmentation pattern obtained from a purified, known sample of ethyl valerate using the GC-MS apparatus described in Example 1.
Figure 9A:
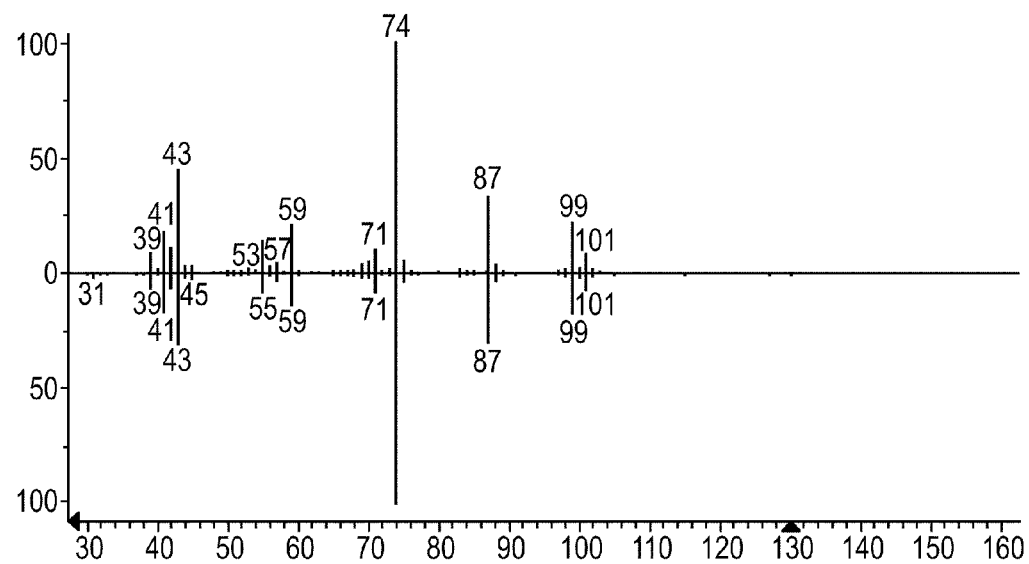
FIG. 9A depicts a mass spectrometry fragmentation pattern (top) for the compound isolated from the headspace and identified as methyl caproate, and the National Institute of Standards and Technology mass spectrometry fragmentation pattern (bottom) for methyl caproate.
Figure 9B:
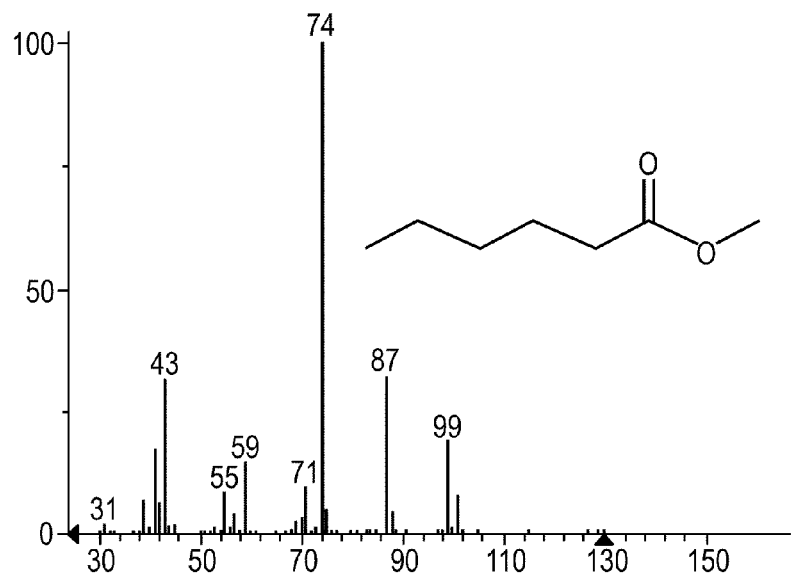
FIG. 9B depicts a mass spectrometry fragmentation pattern obtained from a purified, known sample of methyl caproate using the GC-MS apparatus described in Example 1.
Figure 10A:
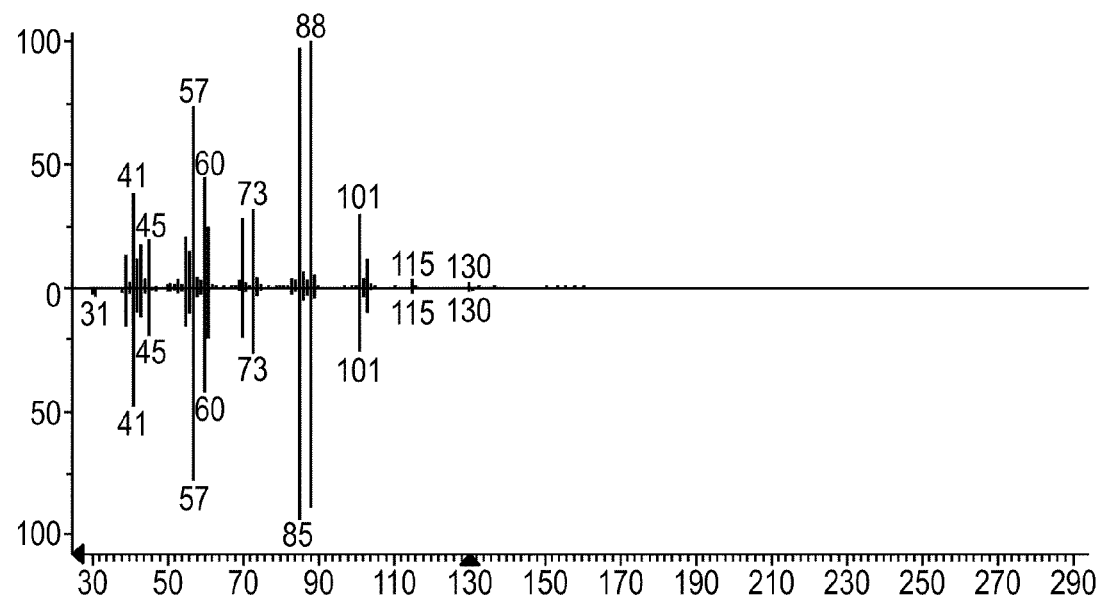
FIG. 10A depicts a mass spectrometry fragmentation pattern (top) for the compound isolated from the headspace and identified as ethyl caproate, and the National Institute of Standards and Technology mass spectrometry fragmentation pattern (bottom) for ethyl caproate.
Figure 10B:
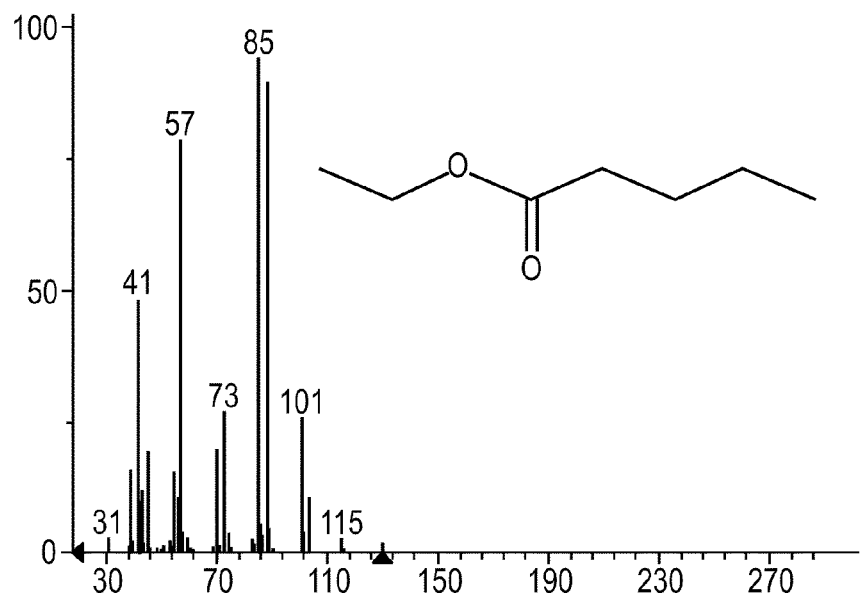
FIG. 10B depicts a mass spectrometry fragmentation pattern obtained from a purified, known sample of ethyl caproate using the GC-MS apparatus described in Example 1.

More specifically, MTb may be identified in a sample by detecting the presence or amount of a VOC associated with the presence or amount of MTb, for example a VOC associated with MTb metabolism. These VOCs include, but are not limited to, ethyl propionate (CAS: 105-37-3), 1-pentanol (CAS: 71-41-0), methyl valerate (CAS: 624-24-8), 1-hexanol (CAS: 111-27-3), ethyl valerate (CAS: 539-82-2), methyl caproate (CAS: 106-70-7), ethyl caproate (CAS: 123-66-0), and/or any of the foregoing compounds in isotopically labeled form. In certain embodiments, the VOCs include, but are not limited to, methoxybenzene (anisole) (CAS: 100-66-3), 2-butanone (CAS: 78-93-3), a chiral version of methyl 2-ethylhexanoate (CAS: 816-19-3), methyl propionate (CAS: 554-12-1), 2-pentanone (CAS: 107-87-9), 3-pentanone (CAS: 96-22-0), 2,4-dimethyl-1-heptene (CAS: 19549-87-2), methyl isobutyl ketone (CAS: 108-10-1), 6-methyl-5-hepten-2-one (CAS: 110-93-0), dimethylsulfoxide (CAS: 67-68-5), dimethylsulfide (CAS: 75-18-3), methyl 2-methylpropionate (CAS: 547-63-7), 1-ethoxy-2-methylpropane (CAS: 627-02-1), 1-ethoxy-butane (CAS: 628-81-9), t-butyl ethyl ether (CAS: 637-92-3), methyl 2-methyl butanoate (868-57-5), isobutanol (CAS: 78-83-1), the aromatic compound represented by the mass spectrum in FIG. 3, and/or any of the foregoing compounds in isotopically labeled form. Any one of or combination of these VOCs may be used to indicate the presence, concentration, and/or state (e.g. viable, growing, etc.) of the MTb and/or related bacterial strains in the sample. Alternatively, the identification of the absence or concentration below a threshold value of one or more of these VOCs can be used to determine the absence of the bacteria in a sample.

1. Sample Collection and Treatment

Samples can be collected as a solid, liquid, and/or gas and can be treated to determine the presence or absence of one or more VOCs indicative of a particular bacteria being present in the sample. A sample can be analyzed directly for one or more VOCs, for example, from the breath of a patient suspected of having a lung infection. Alternatively, the sample can be cultured in a suitable growth medium to allow growth and metabolism of bacteria in the sample. In certain embodiments, the invention involves taking a sputum sample from an individual and placing it in media, for example, with microfluidics, or in culture, for example, with conventional culturing methods. The bacteria, if present, are stimulated to metabolize. The headspace (gaseous phase) generated as a result of this metabolism may be collected, and may be tested for the presence of at least one metabolite indicative of the bacteria in that growth media.

Figure 1A:
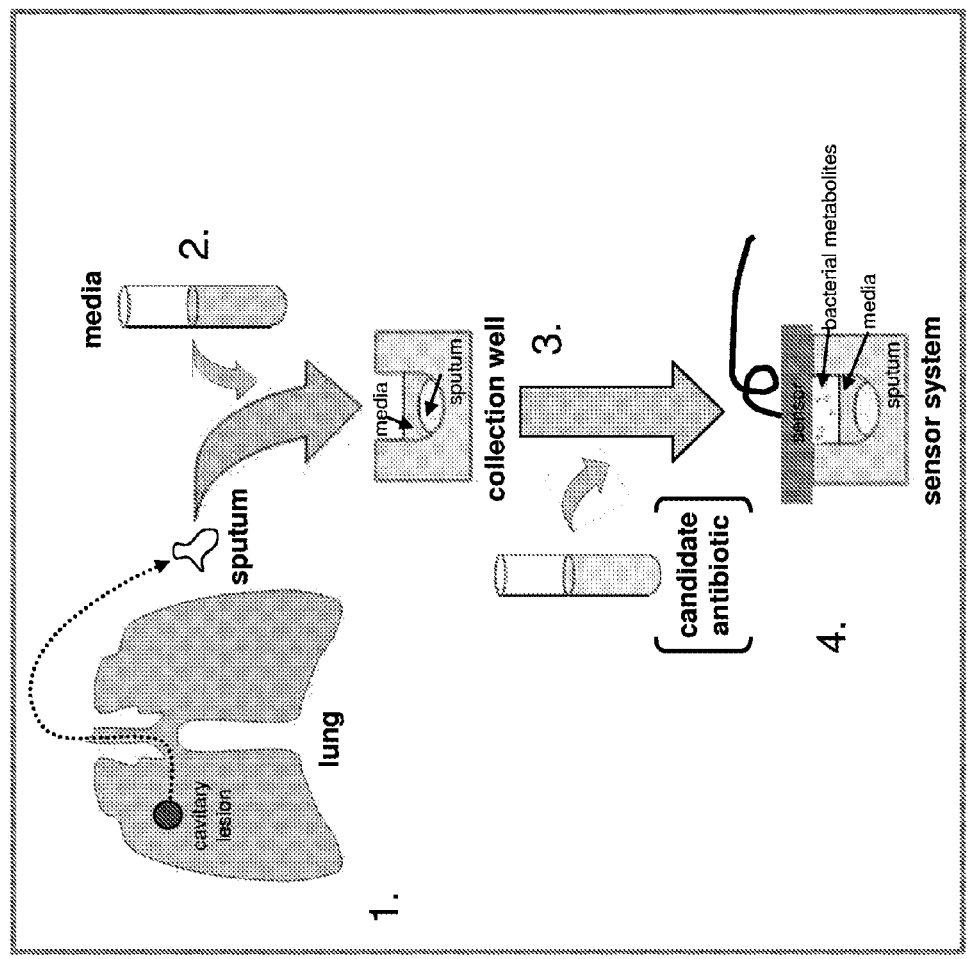
FIG. 1A depicts a flow chart for an embodiment of VOC analysis to rapidly diagnose and determine therapy resistance for tuberculosis.

One exemplary embodiment of sample collection and treatment is depicted in FIG. 1A. In the figure: 1. a sputum sample is collected from a subject suspected of harboring unwanted bacteria (e.g., MTb) in the subject's lungs; 2. the sputum sample is transferred to a collection well and provided with medium to stimulate metabolism of bacteria in the sample; 3. optionally, for samples known to include a particular bacteria, such as MTb, a candidate antibiotic can be added to the sputum and media in the collection well to test for efficacy of an antibiotic or bacterial resistance to an antibiotic; and 4. the collection well is sealed with a detection system sensor and a gas headspace is generated (e.g., from bacterial metabolism). One or more volatile organic compounds in the headspace are detected to diagnose bacterial infection or antibiotic efficacy.

Figure 1B:
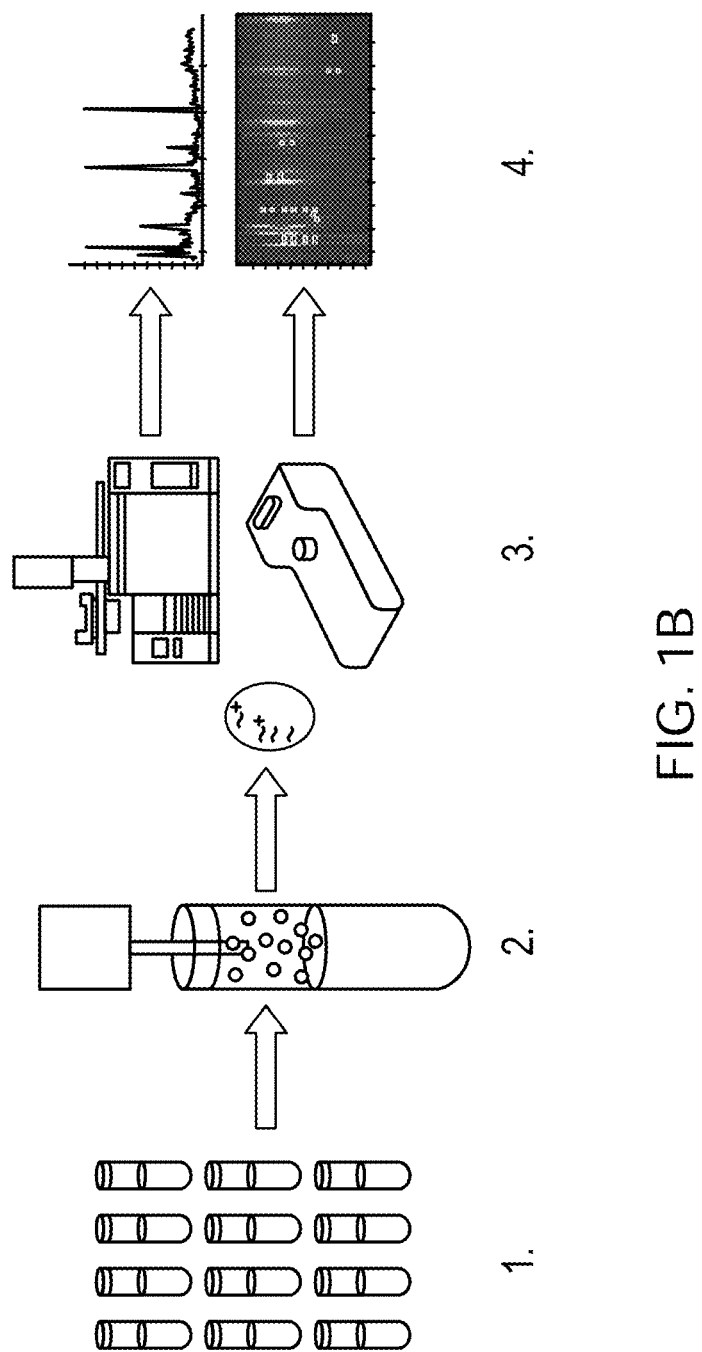
FIG. 1B illustrates an exemplary method for detection of VOCs from the headspace of samples.

A second exemplary embodiment of sample treatment is depicted in FIG. 1B. In the figure: 1. cultured samples are prepared with replicates and matched medium controls; 2. volatile organic compounds in the headspace of the incubated samples are absorbed to concentrating solid phase microextraction (SPME) fiber; 3. the SPME fiber is heated and volatile organic compounds are absorbed into one or more detection systems, for example a GC-MS detection system, a DMS detection system, or a GC-MS/DMS dual system, and data is acquired; and 4. data output is analyzed for features (e.g. one or more VOCs) that distinguish particular bacteria in the sample. When the GC-MS/DMS dual detection is employed, the data from the two systems can be compared to take advantage of database information available from either system.

Samples can be obtained from, for example, biological samples such as exhaled breath directly from an individual or from a breathing machine such as a ventilator, condensate from exhaled breath or a bodily gas, sputum, urine, sweat, blood, plasma, serum, saliva, semen, interstitial fluid, cerebrospinal fluid, dialeysate obtained in kidney dialysis, tears, mucus, amniotic fluid, tissue, gastric lavage, and fecal matter.

In certain embodiments, a detector determines the presence or absence, or alternatively the concentration, of the headspace VOCs in the gas phase to determine whether there are viable bacteria in the sample. Accordingly, the sample container is designed to prohibit the release of gas from the sample container or the introduction of ambient gas into the sample container. If an antibiotic known to inhibit or kill the bacteria is also added to the media, then viable bacteria may indicate the presence of resistant bacteria in the sample. Accordingly, potential antibiotics also may be screened using this method.

The bacteria in a sample may be grown in media or in culture, and the media- or culture-grown bacteria may optionally be exposed to a candidate therapy for treating the bacteria, for example a candidate drug such as an antibiotic. Samples can be cultured for any amount of time that allows for generation of VOCs. For example, samples may be cultured for less than 2 hours, 2-4 hours, 4-6 hours, 6-10 hours, more than 10 hours or more than 24 hours. The culture may include any known bacterial culturing media, for example glucose, lipids, short-chain fatty acids, etc., such as propionate, cholesterol, and/or palmitate. In certain embodiments, the VOCs that are detected are specific for a particular bacteria grown on a particular medium. For example, the method can include collecting a sample that includes a particular bacteria, such as MTb, growing the bacteria on a particular medium, such as sodium propionate, and detecting at least one volatile organic compound indicative of the presence of the bacteria in the sample grown on the particular medium. For example, where *Mycobacterium tuberculosis* is grown on sodium propionate, the organic compound(s) may be or include methyl propionate (CAS: 554-12-1), methyl 2-methylpropionate (CAS: 547-63-7), methyl-2-ethyl hexanoate (816-19-3), and/or the aromatic compound represented by the mass spectrum in FIG. 3. Furthermore, different concentrations of the propionate, and/or mixtures of propionate with other carbon sources, can be included in the growth medium to optimize detection and/or generation of particular VOCs that can be used to detect the presence of or quantitate particular bacteria (e.g., MTb) in a sample. In other embodiments, the VOCs that are detected are the same VOCs regardless of the media components. In certain other embodiments, the bacterial culturing media contains an isotopically labeled compound, such as a compound enriched is $^{13}C$, e.g., $^{13}C$-labeled propionate.

2. Volatile Organic Compound Detection

The one or more VOCs may be detected using various technologies including, but not limited to: gas chromatography (GC); spectrometry, for example mass spectrometry (including quadrapole, time of flight, tandem mass spectrometry, ion cyclotron resonance, and/or sector (magnetic and/or electrostatic)), ion mobility spectrometry, field asymmetric ion mobility spectrometry, and/or DMS; fuel cell electrodes; light absorption spectroscopy; nanoparticle technology; flexural plate wave (FPW) sensors; biosensors that mimic naturally occurring cellular mechanisms; electrochemical sensors; photoacoustic equipment; laser-based equipment; electronic noses (bio-derived, surface coated); various ionization techniques; and/or trained animal detection.

In various embodiments, the present invention is an improvement over the existing methods for bacterial detection. For example, the sputum smear method of MTb detection is dependent on microscopy to detect the presence of MTb and has a lower limit of detection of 10,000 MTb bacilli/mL and culture methods have a lower limit of detection of $10^5$-$10^6$ bacilli/mL. However, embodiments of the present invention do not require microscopy and have lower limits of detection as low as $10^3$ bacilli/mL. One particular advantage of embodiments of the present invention over standard culturing methods is the amount time for analysis. It typically takes as long as 1-4 weeks to determine TB presence or resistance by current culture methods, whereas both the volatile analysis of sputum and breath samples may yield a result in minutes to hours. To the extent that a sample is cultured to generate VOCs above the culture surface, an adequate culture may be obtained in a matter of hours or days, not weeks as with current methods. In addition, embodiments of the present invention allow for rapid detection of drug resistance if bacterial growth is measured despite the addition of antibiotic. Because embodiments of the present invention utilize the detection of VOCs associated with living bacteria, they also have the ability to increase sensitivity and selectivity. The selectivity derives from the fact that only live bacteria will be actively metabolizing and thus will give a signature, as opposed to serology or other similar techniques that are sensitive but do not distinguish past from present exposure. The increased sensitivity over other methods such as smear microscopy comes from the ability of current ion mass analyzers to detect in the parts per million down to parts per trillion range of sensitivity. Thus, having the known identity of a volatilized compound will enable the exploitation of the increased sensitivities of these mass analyzers.

In certain embodiments, a point-of-care diagnostic tool is used to identify bacterial VOC biomarkers. A point-of-care diagnostic tool, such as a micromachined DMS, preferably is portable and may detect VOCs to low limits of detection. Accordingly, in certain embodiments, the present invention includes a library of VOC data and relevant information for a point-of-care diagnostic tool that may be used to identify bacteria in a sample obtained from one or more sources.

2A. Differential Mobility Spectrometry

In certain embodiments, the diagnostic tool used to detect the one or more VOCs is a differential mobility spectrometer (Model SVAC, Sionex Corporation, Bedford, Mass.) ("DMS" or "DMS device"). A DMS device can operate at ambient temperature and pressure. A micromachined DMS device has been developed as a portable unit that is mobile and hand-held. The spectrometer produces spectra that differentiates between compounds that may co-elute in a GC-MS system, often yielding an improved ability to identify VOCs in a sample. For matrix-assisted laser desorption ionization/mass spectrometry (MALDI-MS), a statistical model has demonstrated the ability to distinguish between roughly 10 species similar to *B. subtilis* when the spectral masses are grouped in 1.5 Daltons (Da) ranges. This is due to roughly the same number of proteins per unit-mass interval. Recent data also suggests a 75% correct identification rate using MALDI-MS with no false positives. However, with the DMS technology, even larger numbers of species may be easily distinguished, as the spectra may be more easily deconvoluted than those of MS due to differing ion mobilities.

DMS devices are quantitative and can have extremely sensitive detection limits, down to the parts-per-trillion range. DMS technology uses the non-linear mobility dependence of ions on high strength RF electric fields for ion filtering, and operates in air at atmospheric pressure. DMS technology enables the rapid detection and identification of compounds that typically cannot be resolved by other analytical techniques. DMS devices scale down well, allowing miniaturization of the analytical cell using MicroElectroMechanical (MEMS) fabrication, while preserving sensitivity and resolution. These and other advantages of a DMS device make it attractive as a quantitative detector that is sufficiently low in cost to be practical for use in the field, for example in point-of-care diagnostics in clinical settings.

Conceptually, the operating principle of a DMS device is similar to that of a quadrupole mass spectrometer, with the significant distinction that it operates at atmospheric pressure so it measures ion mobility rather than ion mass. Mobility is a measure of how easily an ion travels through the air in response to an applied force, and is dependent on the size, charge and mass of the ion. A DMS spectrometer acts as a tunable ion filter.

To perform a measurement, a gas sample is introduced into the spectrometer, where it is ionized, and the ions are transported through an ion filter towards the detecting electrodes (Faraday plates) by a carrier gas. The DMS device can separate chemical components of a substance based on differing ion mobilities.

2.B. Data Libraries

In certain embodiments, the diagnostic device (e.g. a GC-MS device, a DMS device, a GC-MS/DMS dual system, or any of the devices described above) can include electronics capable of storing a library of information about VOCs that are indicative of various microorganisms. Alternatively, the electronics can allow for connectivity to one or more remote databases. In the library or databases, previously collected and/or known VOC data, e.g. GC-MS and/or DMS spectral patterns, may be associated with certain microorganisms and/or include associations with other relevant information. Other relevant information may include, for example, information about culturing conditions (e.g. media, media components, temperature, and/or headspace gases above the culture) of a sample that undergoes a culturing step, information about the bodily source of a sample obtained from the body (e.g. tissue type or bodily fluid type), information about the environmental source of a sample obtained from the environment (e.g. soil type or liquid type), and information about an industrial setting that is the source of the sample (e.g. likely contaminants and nutrient sources). Such information may be used in a portable device for the rapid delivery of results that identify particular microorganisms in a sample.

Additional features relating to methods for detecting one or more volatile organic compounds are described in U.S. Patent Application Publication No. 2009/0239252, which is hereby incorporated by reference for all purposes.

3. Methods and Devices for Identifying *Mycobacterium Tuberculosis*

One aspect of the invention provides a method for identifying *Mycobacterium tuberculosis* bacteria in a sample. The method comprises detecting one or more volatile organic compounds indicative of a presence of or response to treatment or resistance of the *Mycobacterium tuberculosis* bacteria in the sample, the one or more volatile organic compounds being selected from the group consisting of ethyl propionate, 1-pentanol, methyl valerate, 1-hexanol, ethyl valerate, methyl caproate, ethyl caproate, and any of the foregoing compounds in isotopically labeled form. Detection of one or more of the volatile organic compounds indicates that *Mycobacterium tuberculosis* bacteria is present in the sample.

In certain embodiments, the one or more volatile organic compounds comprises methyl caproate. In certain other embodiments, the one or more volatile organic compounds comprises 1-hexanol. In certain other embodiments, the one or more volatile organic compounds comprises ethyl propionate. In certain other embodiments, the one or more volatile organic compounds comprises 1-pentanol. In certain other embodiments, the one or more volatile organic compounds comprises methyl valerate. In certain other embodiments, the one or more volatile organic compounds comprises ethyl valerate. In certain other embodiments, the one or more volatile organic compounds comprises ethyl caproate. In certain other embodiments, the one or more volatile organic compounds is selected from the group consisting of ethyl propionate, 1-pentanol, methyl valerate, 1-hexanol, ethyl valerate, methyl caproate, and ethyl caproate.

In certain embodiments, a combination of two or more volatile organic compounds is indicative of the presence of or response to treatment or resistance of *Mycobacterium tuberculosis* in the sample. In certain embodiments, the one or more volatile organic compounds comprises methyl caproate and 1-hexanol.

In certain embodiments, the method further comprises collecting from a subject a sample suspected of comprising *Mycobacterium tuberculosis* bacteria.

In certain embodiments, the method further comprises detecting one or more volatile organic compounds indicative of a presence of or response to treatment or resistance of the *Mycobacterium tuberculosis* bacteria in the sample, the one or more volatile organic compounds being selected from the group consisting of methoxybenzene (anisole), 2-butanone, methyl 2-ethylhexanoate, a chiral version of methyl 2-ethylhexanoate, methyl propionate, 2-pentanone, 3-pentanone, 2,4-dimethyl-1-heptene, methyl isobutyl ketone, 6-methyl-5-hepten-2-one, dimethylsulfoxide, dimethylsulfide, methyl 2-methylpropionate, 1-ethoxy-2-methylpropane, 1-ethoxybutane, t-butyl ethyl ether, isobutanol, and any of the foregoing compounds in isotopically labeled form. In certain other embodiments, the method comprises detecting methyl caproate and methyl propionate.

In certain embodiments, the sample was exposed to a candidate therapy for treating *Mycobacterium tuberculosis*. In certain embodiments, the sample comprises exhaled breath from an individual. In certain embodiments, sample is selected from the group consisting of sputum, blood, urine, pleural fluid, gastric lavage, and pleural biopsy tissue. In certain other embodiments, sample is sputum.

In certain embodiments, an amount of one or more volatile organic compounds is detected. In certain embodiments, the detecting is performed using a portable device. In certain embodiments, the detecting is performed using a differential mobility spectrometer.

Another aspect of the invention provides a method for identifying *Mycobacterium tuberculosis* bacteria in a sample. The method comprises: (a) culturing a sample in a media comprising an alkali metal propionate, an alkali metal pentanoate, an alkali metal hexanoate, cholesterol, or any of the foregoing compounds in isotopically labeled form; and (b) detecting one or more volatile organic compounds indicative of a presence of or response to treatment or resistance of the *Mycobacterium tuberculosis* bacteria from the cultured sample, the one or more volatile organic compounds being selected from the group consisting of ethyl propionate, 1-pentanol, methyl valerate, 1-hexanol, ethyl valerate, methyl caproate, ethyl caproate, and any of the foregoing compounds in isotopically labeled form.

In certain embodiments, the method comprises culturing a sample in a media comprising an alkali metal propionate, an alkali metal pentanoate, an alkali metal hexanoate, and cholesterol. In certain other embodiments, the method comprises culturing a sample in a media comprising an alkali metal propionate.

In certain embodiments, the one or more volatile organic compounds comprises methyl caproate. In certain other embodiments, the one or more volatile organic compounds comprises 1-hexanol. In certain other embodiments, the one or more volatile organic compounds comprises ethyl propionate. In certain other embodiments, the one or more volatile organic compounds comprises 1-pentanol. In certain other embodiments, the one or more volatile organic compounds comprises methyl valerate. In certain other embodiments, the one or more volatile organic compounds comprises ethyl valerate. In certain other embodiments, the one or more volatile organic compounds comprises ethyl caproate. In certain other embodiments, the one or more volatile organic compounds is selected from the group consisting of ethyl propionate, 1-pentanol, methyl valerate, 1-hexanol, ethyl valerate, methyl caproate, and ethyl caproate.

In certain embodiments, a combination of two or more volatile organic compounds is indicative of the presence of or response to treatment or resistance of *Mycobacterium tuberculosis* from the cultured sample. In certain embodiments, the one or more volatile organic compounds comprises methyl caproate and 1-hexanol.

In certain embodiments, the method further comprises collecting from a subject a sample suspected of comprising *Mycobacterium tuberculosis* bacteria.

In certain embodiments, the method further comprises detecting one or more volatile organic compounds indicative of a presence of or response to treatment or resistance of the *Mycobacterium tuberculosis* bacteria in the sample, the one or more volatile organic compounds being selected from the group consisting of methoxybenzene (anisole), 2-butanone, methyl 2-ethylhexanoate, a chiral version of methyl 2-ethylhexanoate, methyl propionate, 2-pentanone, 3-pentanone, 2,4-dimethyl-1-heptene, methyl isobutyl ketone, 6-methyl-5-hepten-2-one, dimethylsulfoxide, dimethylsulfide, methyl 2-methylpropionate, 1-ethoxy-2-methylpropane, 1-ethoxybutane, t-butyl ethyl ether, isobutanol, and any of the foregoing compounds in isotopically labeled form. In certain other embodiments, the method comprises detecting methyl caproate and methyl propionate.

In certain embodiments, the sample was exposed to a candidate therapy for treating *Mycobacterium tuberculosis*. In certain embodiments, the sample comprises exhaled breath from an individual. In certain embodiments, sample is selected from the group consisting of sputum, blood, urine, pleural fluid, gastric lavage, and pleural biopsy tissue. In certain embodiments, sample is sputum.

In certain embodiment, the method further comprises extracting the one or more volatile organic compounds from the culture by solid phase microextraction from a headspace of the culture or thermal desorption from a headspace of the culture to provide a more concentrated sample of the one or more volatile organic compounds for detection.

In certain embodiments, an amount of one or more volatile organic compounds is detected. In certain embodiments, the detecting is performed using a portable device. In certain embodiments, the detecting is performed using a differential mobility spectrometer.

In certain embodiments, one or more of the alkali metal propionate, an alkali metal pentanoate, an alkali metal hexanoate, cholesterol are isotopically labeled (i.e., isotopically enriched) with carbon-13.

Another aspect of the invention provides a method for identifying *Mycobacterium tuberculosis* bacteria in a sample. The method comprises: (a) collecting a sample suspected of comprising *Mycobacterium tuberculosis* bacteria; (b) culturing the sample using a media comprising at least two compounds selected from the group consisting of cholesterol, sodium propionate, sodium pentanoate, sodium hexanoate, and any of the foregoing compounds in isotopically labeled form; and (c) detecting one or more volatile organic compounds associated with *Mycobacterium tuberculosis* metabolism and indicative of a presence of or response to treatment or resistance of the *Mycobacterium tuberculosis* bacteria in the cultured sample.

Another aspect of the invention provides a method for detecting a strain of *Mycobacterium tuberculosis* that is resistant to antibiotic treatment. The method comprises exposing a strain of *Mycobacterium tuberculosis* to an antibiotic agent, then using one of the methods described herein to determine if said strain of *Mycobacterium tuberculosis* is still present after being exposed to said antibiotic agent. In certain embodiments, the antibiotic agent is isoniazid (INH) or rifampicin (RIF).

Another aspect of the invention provides a device for identifying *Mycobacterium tuberculosis* bacteria in a sample. The device comprises: (a) an input for receiving a sample suspected of comprising *Mycobacterium tuberculosis* bacteria; and (b) a means for detecting one or more volatile organic compounds indicative of a presence of or response to treatment or resistance of the *Mycobacterium tuberculosis* bacteria in the sample, the one or more volatile organic compounds being selected from the group consisting of ethyl propionate, 1-pentanol, methyl valerate, 1-hexanol, ethyl valerate, methyl caproate, ethyl caproate, and any of the foregoing compounds in isotopically labeled form.

In certain embodiments, the device further comprises a means for extracting one or more volatile organic compounds from the sample. In certain embodiments, the device further comprises means for detecting one or more volatile organic compounds selected from the group consisting of methoxybenzene (anisole), 2-butanone, methyl 2-ethylhexanoate, a chiral version of methyl 2-ethylhexanoate, methyl propionate, 2-pentanone, 3-pentanone, 2,4-dimethyl-1-heptene, methyl isobutyl ketone, 6-methyl-5-hepten-2-one, dimethylsulfoxide, dimethylsulfide, 1-ethoxy-2-methylpropane, 1-ethoxybutane, t-butyl ethyl ether, isobutanol, and any of the foregoing compounds in isotopically labeled form.

Various aspects and embodiments of are described above. The embodiments can be combined in various ways to embrace the multiple features of the invention. All combinations and permutations of the various aspects and embodiments are contemplated.

EXAMPLES

Example 1

Exemplary Method for Identifying and Detecting Exemplary Volatile Organic Compounds in a Headspace Sample Following Incubation of *Mycobacterium tuberculosis*

General Experimental Procedure:

*Mycobacterium tuberculosis* RV laboratory strain (Mtb RV strain) was incubated in a minimal media containing four carbon sources (cholesterol 0.01% w/v, sodium propionate 0.1% w/v, sodium pentanoate (valerate) 0.1% w/v, and sodium hexanoate (caproate) 0.1% w/v). Then, the Mtb RV strain was resuspended in the media and the headspace was incubated for 24 h at 37° C. Following this incubation the headspace was extracted for 30 minutes onto a SPME fiber (PDMS/DVB/Carboxen) that was then analyzed on a dual GC-MS/DMS instrument. This experiment was repeated three times with 5 replicates/sample. Samples containing media alone were compared to samples containing the Mtb. Peaks that were present in the Mtb containing samples but not media alone were identified using a National Institute of Standards and Technology (NIST) library. Purified standards were then purchased and run on the instrument to confirm compound structure and retention time.

Figure 2:
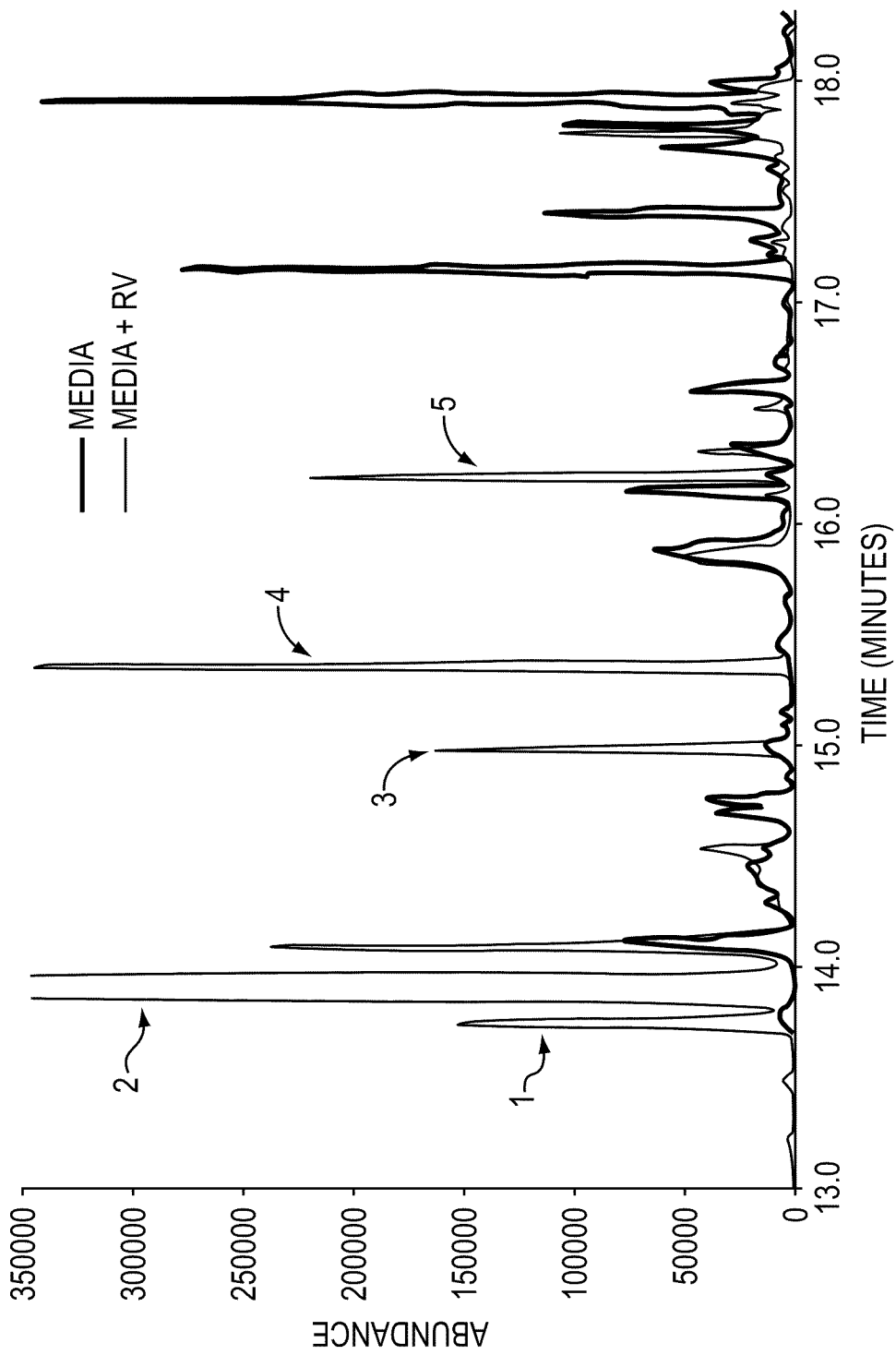
FIG. 2 depicts a GC-MS total ion chromatograph of a sample from the headspace following incubation of *Mycobacterium tuberculosis* RV laboratory strain. The chromatograph shows peaks corresponding to 1) methyl pentanoate, 2) 1-hexanol, 3) ethyl pentanoate, 4) methyl hexanoate, and 5) ethyl hexanoate, as explained in Example 1.

Results:

Analytical analysis identified the presence of the volatile organic compounds listed in Table 1 below. The CAS registry number for each compound and the gas chromatograph retention time for each compound is presented in Table 1. A GC-MS total ion chromatograph showing peaks corresponding to methyl pentanoate, 1-hexanol, ethyl pentanoate, methyl hexanoate, and ethyl hexanoate is depicted in FIG. 2. The data indicate the presence of ethyl propionate, 1-pentanol, methyl valerate, 1-hexanol, ethyl valerate, methyl caproate, and ethyl caproate in the headspace following incubation of the Mtb RV strain. In addition, the mass spectrometry ion fragmentation pattern of ethyl propionate, 1-pentanol, methyl valerate, 1-hexanol, ethyl valerate, methyl caproate, and ethyl caproate, as isolated from the headspace, is depicted as the top fragmentation pattern in FIGS. 4A-10A, while the mass spectrometry fragmentation pattern from the National Institute of Standards and Technology for these compounds is depicted as the bottom fragmentation pattern in FIGS. 4A-10A, respectively. Further, FIGS. 4B-10B show the mass spectrometry fragmentation patterns of known samples of ethyl propionate, 1-pentanol, methyl valerate, 1-hexanol, ethyl valerate, methyl caproate, and ethyl caproate, respectively, as observed on our GC-MS instrument.

TABLE 1

| Compound | RT (min) | CAS # |
| --- | --- | --- |
| ethyl propionate | 10.97 | 105-37-3 |
| 1-pentanol | 11.5 | 71-41-0 |
| methyl valerate | 13.73 | 624-24-8 |
| 1-hexanol | 13.92 | 111-27-3 |
| ethyl valerate | 14.97 | 539-82-2 |
| methyl caproate | 15.34 | 106-70-7 |
| ethyl caproate | 16.19 | 123-66-0 |

Example 2

Further Exemplary Method for Identifying and Detecting Exemplary Volatile Organic Compounds in a Headspace Sample Following Incubation of *Mycobacterium Tuberculosis*

General Experimental Procedure:

An Mtb culture and *M. smegmatis* culture (control) were incubated in minimal media containing sodium propionate. After the cultures incubated for 24 hours, the volatile organic compounds (VOCs) were extracted from the headspace using solid phase micro-extraction (SPME) fibers. SPME fibers are coated fibers that specifically extract volatiles from the air. See, for example, Pawliszyn Janusz in *Solid Phase Microextraction: Theory and Practice* (1997, Wiley-VCH) for a further description. Next, the fibers were irradiated with UV light to kill any live bacteria, and then the fibers were packaged on ice and shipped overnight to an analytical laboratory for analysis.

Compounds adsorbed on the fiber were desorbed in the injection port of a gas chromatograph (GC) and detected by both mass spectrometry (MS) and differential mobility spectrometry (DMS). The identities of the VOCs were established using MS data. In particular, in order to facilitate identification and validation of Mtb-specific VOCs discovered in the DMS spectra, a dual detection system incorporating a MS was implemented using the arrangement illustrated in FIG. 1B. Cryogenic focusing was applied at the proximal end of the GC column to facilitate the analysis of complex mixtures of compounds (>50 compounds/sample) by improving chromatographic resolution of the VOCs. The GC was fitted with a column chosen based on its ability to effectively separate typical volatile organic compounds. The distal end of the column was connected to two guard columns by a Y-connector in order to simultaneous transfer the column eluent to the DMS and MS. Flow rates were measured to confirm that the eluent was evenly distributed to both sensor platforms. Recording of the MS and DMS data was simultaneously triggered upon introduction of the sample in the GC injection port to ensure synchronized data collection by the MS and DMS software.

Compound analyte retention times observed in the MS and the DMS data were similar. The relative standard deviation of this variance was consistently less than 5%.

Figure 11:
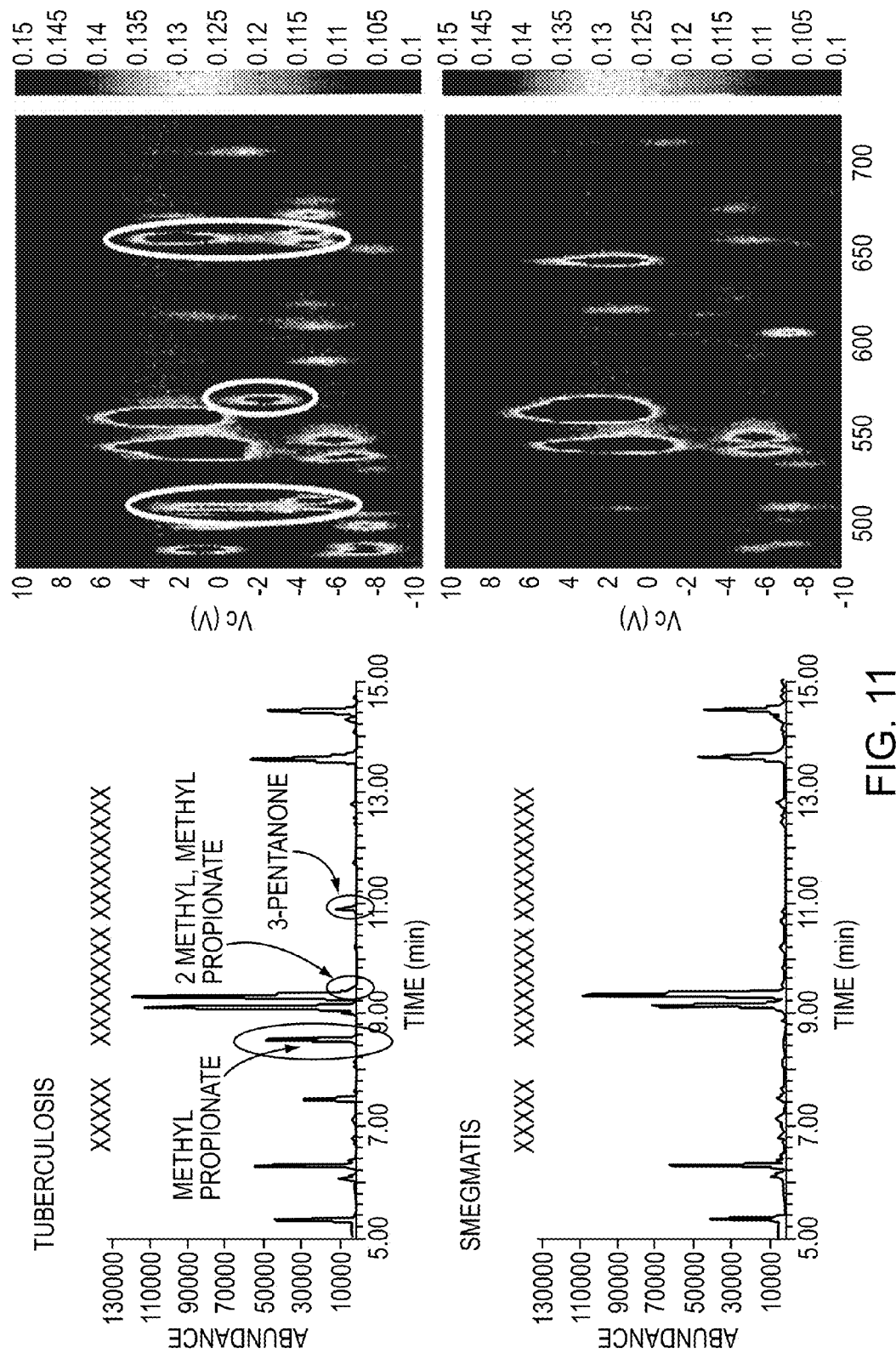
FIG. 11 depicts i) Top Left: a GC-MS total ion chromatograph of a sample from the headspace following incubation of *Mycobacterium tuberculosis*, ii) Top Right: a plot of DMS data obtained from a sample from the headspace following incubation of *Mycobacterium tuberculosis*, iii) Bottom Left: a GC-MS total ion chromatograph of a sample from the headspace following incubation of *Mycobacterium smegmatis*, and iv) Bottom Right: a plot of DMS data obtained from a sample from the headspace following incubation of *Mycobacterium smegmatis*, as explained in Example 2.

Results:

Analytical analysis identified the presence of methyl propionate, 2-methyl, methyl propionate, and 3-pentanone from the headspace of the Mtb culture. These compounds were not detected from the headspace of the *M. smegmatis* (control) culture. Mass spectral data and DMS data for samples taken from the headspace of the Mtb culture and the *M. smegmatis* (control) culture are provided in FIG. 11. The GC-MS total ion chromatographs plot abundance of the VOC biomarker compound versus gas chromatograph retention time (minutes).

Example 3

Identification of Volatile Organic Compounds in a Headspace Sample Following Incubation of Four Clinical Strains of *Mycobacterium Tuberculosis*

General Experimental Procedure:

Four clinical strains of Mtb were grown to a concentration of $10^8$ bacilli/mL and re-suspended in minimal media containing sodium propionate, cholesterol, sodium pentanoate, and sodium hexanoate. After the bacteria were incubated for 24 hours, volatile organic compounds (VOCs) were extracted from the headspace and analyzed according to the general experimental procedures described in Examples 1 and 2. The four clinical strains of Mtb used in this experiment were i) CDC1551 which is a virulent clinical strain from lineage 4 (See, Gagneux et al. in *Lancet Infect. Dis.* (2007) vol. 7, pages 328-337), ii) HN878 which is a strain from East Asia that is also known as the "Beijing" strain (See, Gagneux et al. in *Lancet Infect. Dis.* (2007) vol. 7, pages 328-337), iii) 6-247 which is a clinically derived strain of Mtb from Mexico furnished by our collaborators at University of Texas-Brownsville, and iv) 6-2342B which is a clinically derived strain of Mtb from Mexico furnished by our collaborators at University of Texas-Brownsville.

Figure 12:
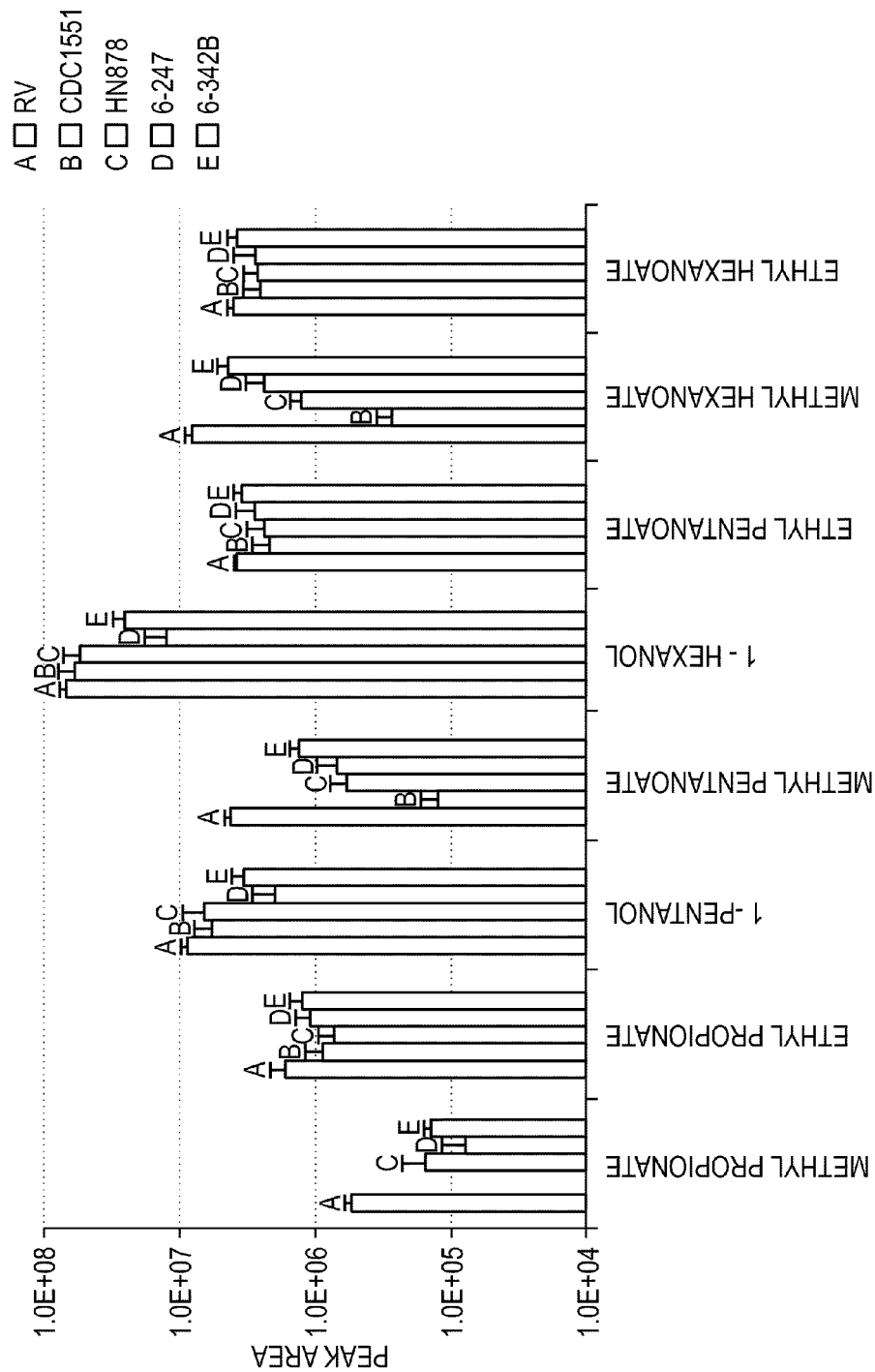
FIG. 12 is a chart showing the peak area for VOCs in the GC-MS total ion chromatograph of a sample isolated from the headspace of the cultures from four clinical strains of Mtb and the Mtb RV laboratory strain, as explained in Example 3.

Results:

Analytical analysis identified the presence of methyl propionate, ethyl propionate, 1-pentanol, methyl pentanoate, 1-hexanol, ethyl pentanoate, methyl hexanoate, and ethyl hexanoate from the headspace of each Mtb culture. FIG. 12 is a chart showing peak areas for the identified VOCs in the GC-MS total ion chromatograph of samples isolated from the headspace of the cultures. The data in FIG. 12 show that all four clinical strains and the lab strain RV expressed the identified VOCs with similar abundances as measured by the mass spectrometry peak area, which is a quantitative assessment of the abundance of each compound.

Example 4

Identification of Volatile Organic Compounds in a Headspace Sample Following Incubation of *Mycobacterium Tuberculosis, Mycobacterium Smegmatis, Mycobacterium Fortuitum*, and *Escherichia Coli*

General Experimental Procedure:

Cultures of *Mycobacterium tuberculosis* RV laboratory strain, *Mycobacterium smegmatis, Mycobacterium fortuitum*, and *Escherichia coli* were grown to a concentration of $10^8$ bacilli/mL. After the bacteria were incubated for 24 hours in minimal media containing sodium propionate, cholesterol, sodium pentanoate, and sodium hexanoate, the volatile organic compounds (VOCs) were extracted from the headspace and analyzed according to the general experimental procedures described in Example 2.

Figure 13:
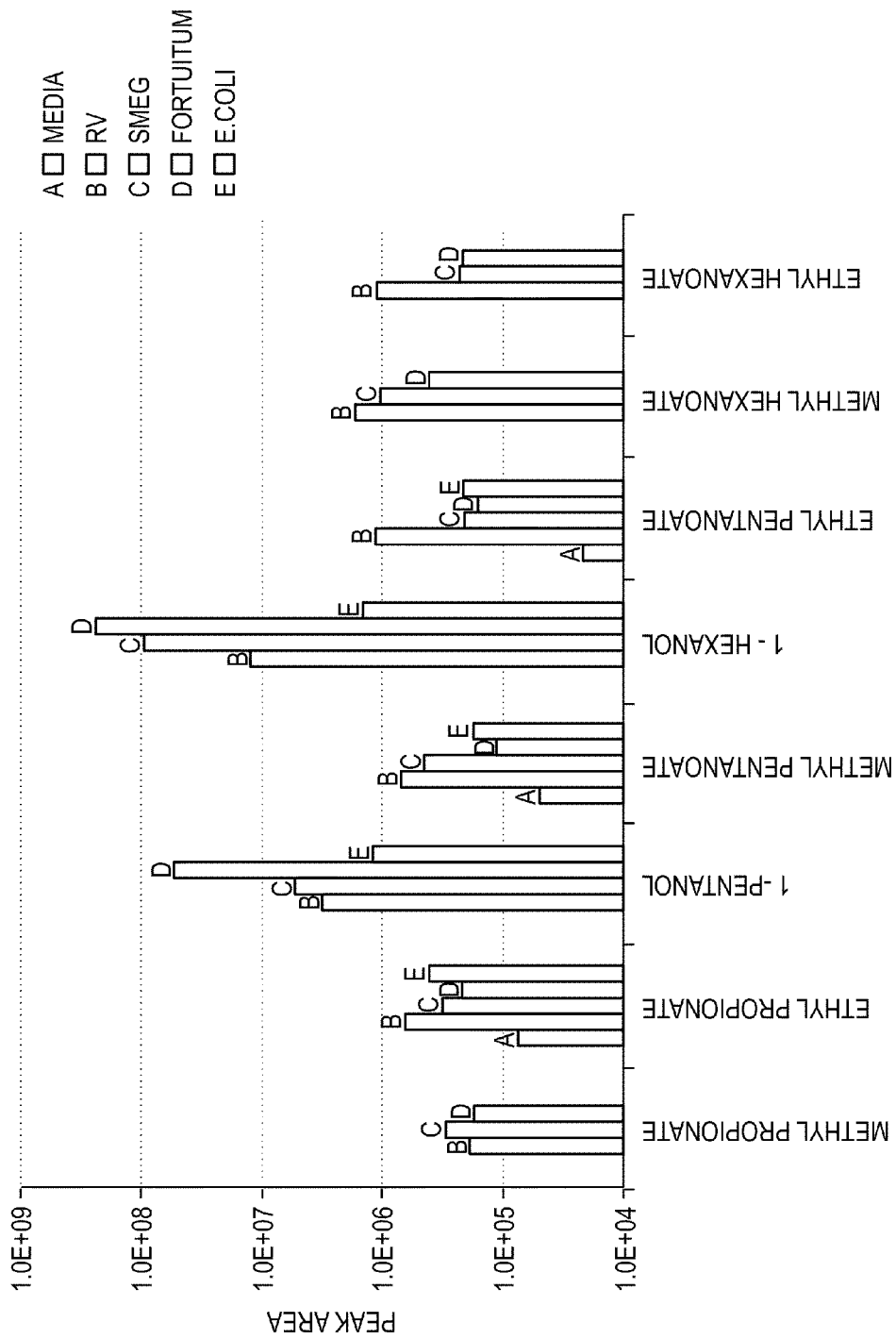
FIG. 13 is a chart showing the peak area for the identified VOCs in the GC-MS total ion chromatograph of samples isolated from the headspace of bacteria cultures, as explained in Example 4.
Figure 14:
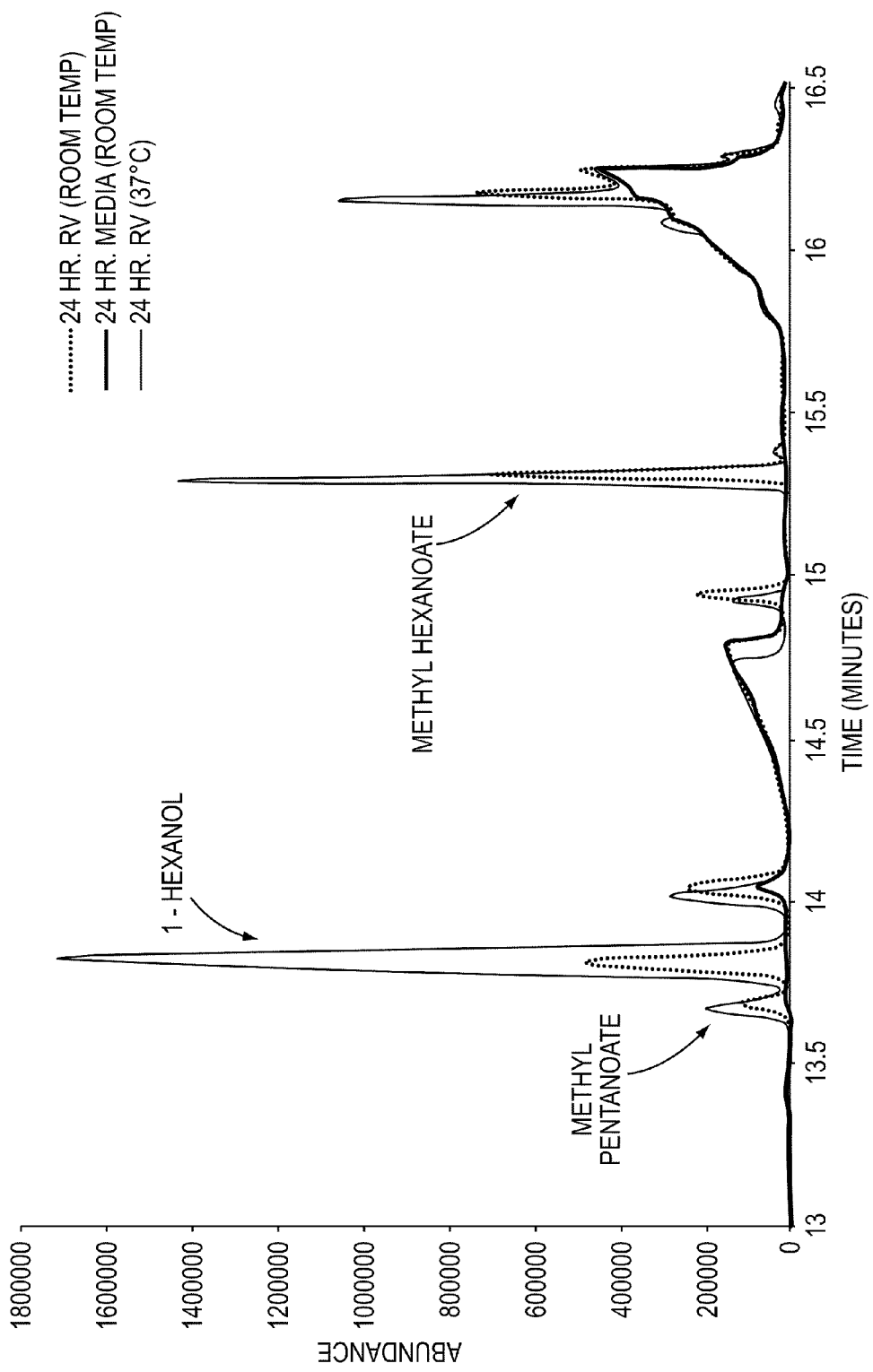
FIG. 14 is an overlay of i) a GC-MS total ion chromatograph of a sample isolated from the headspace of a Mtb RV culture performed at 37° C., ii) a GC-MS total ion chromatograph of a sample isolated from the headspace of a Mtb RV culture performed at 27° C., and iii) a GC-MS total ion chromatograph of a sample isolated from the headspace of a culture containing just media, as explained in Example 5.
Figure 15:
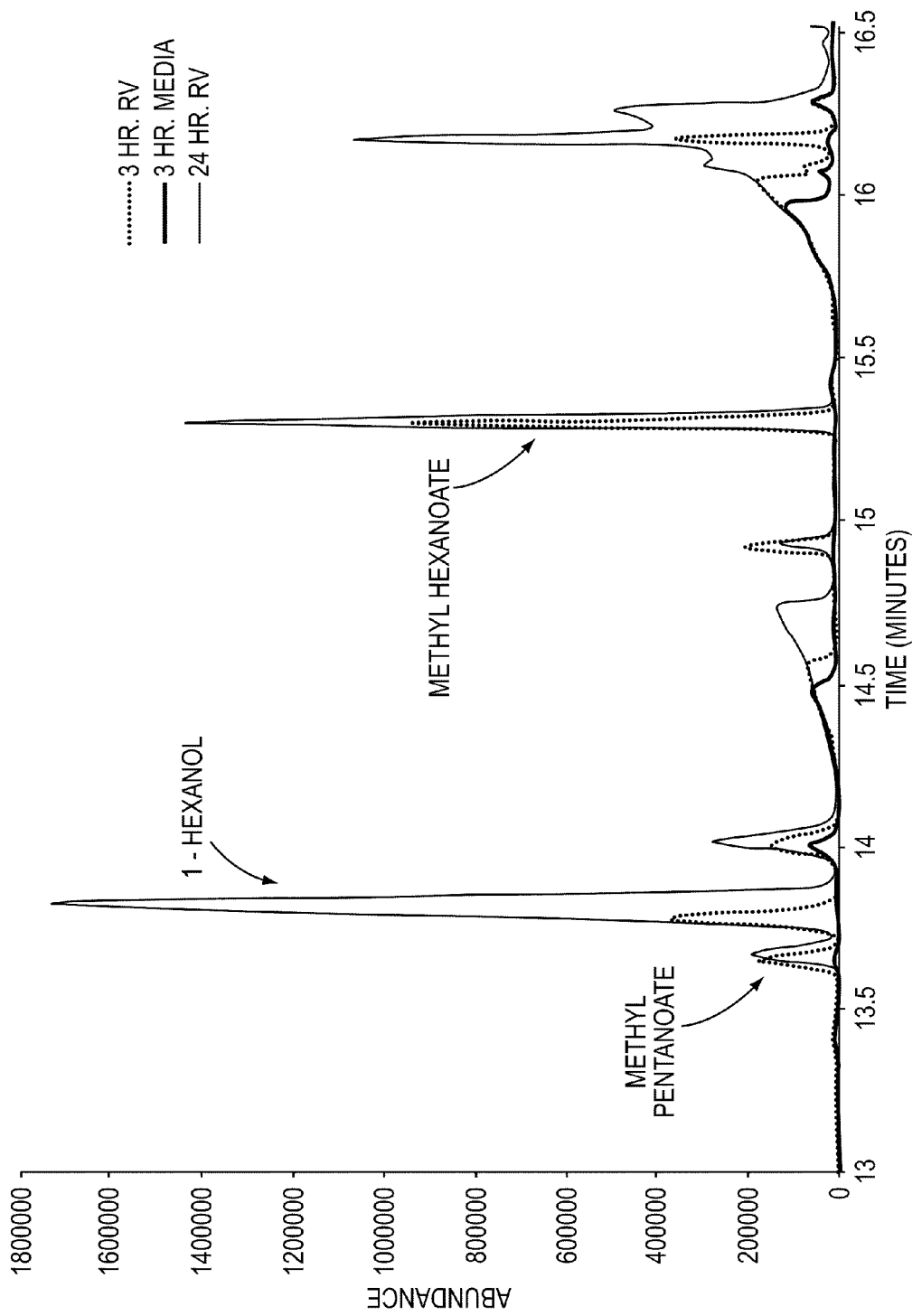
FIG. 15 is an overlay of i) a GC-MS total ion chromatograph of a sample isolated from the headspace of a Mtb RV culture after incubation for 3 hours, ii) a GC-MS total ion chromatograph of a sample isolated from the headspace of a culture containing just media after incubation for 3 hours, and iii) a GC-MS total ion chromatograph of a sample isolated from the headspace of a Mtb RV culture after incubation for 24 hours, as explained in Example 5.
Figure 16:
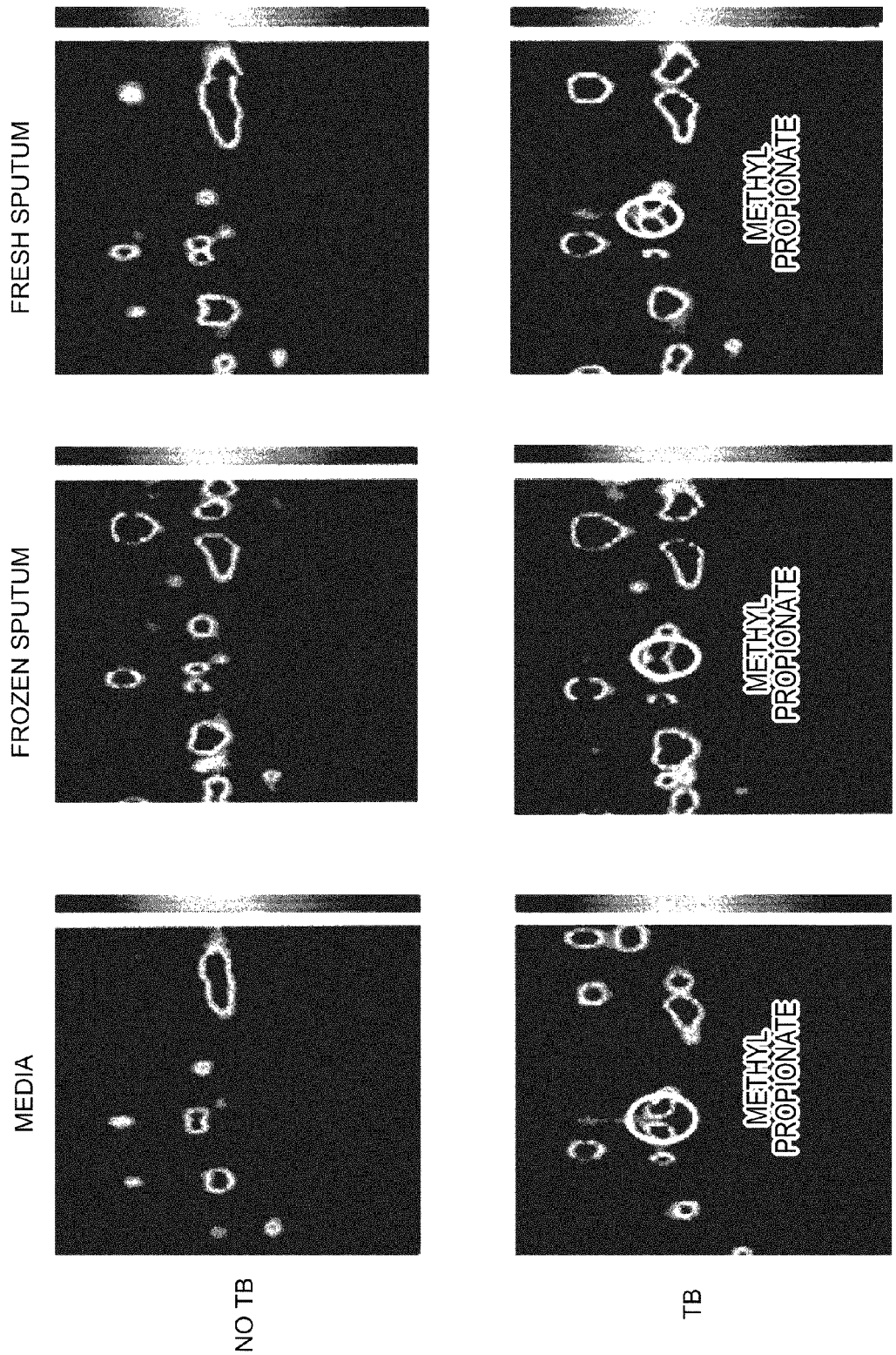
FIG. 16 shows plots of DMS data obtained in Example 6.
Figure 17:
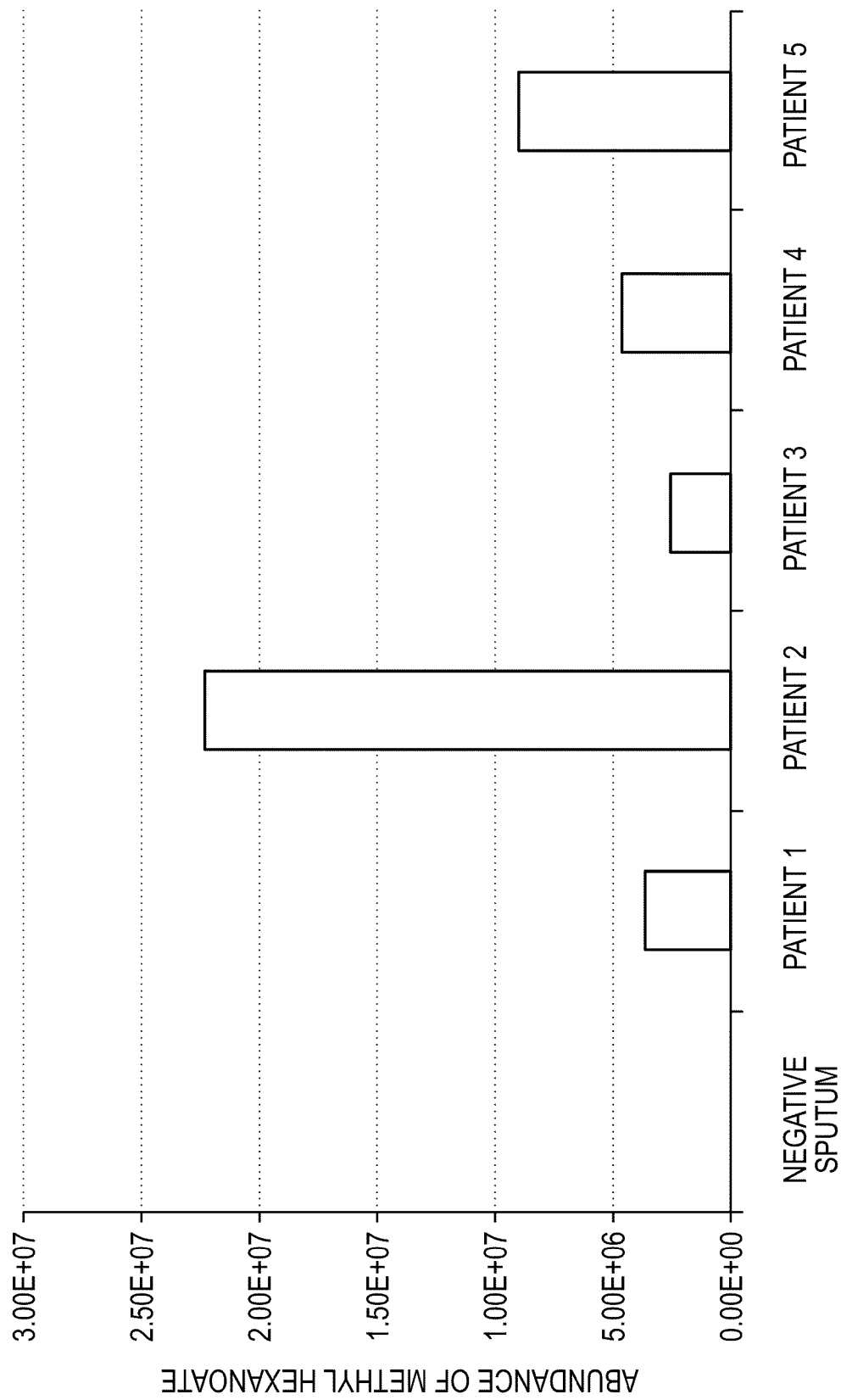
FIG. 17 is a graph showing i) the abundance of methyl hexanoate in samples from the headspace of sputum cultures from five different patients with Mtb, and ii) the abundance of methyl hexanoate a sample from the headspace of a culture of pooled sputum (i.e., negative sputum) from patients confirmed not to be infected with Mtb, as explained in Example 7.
Figure 18:
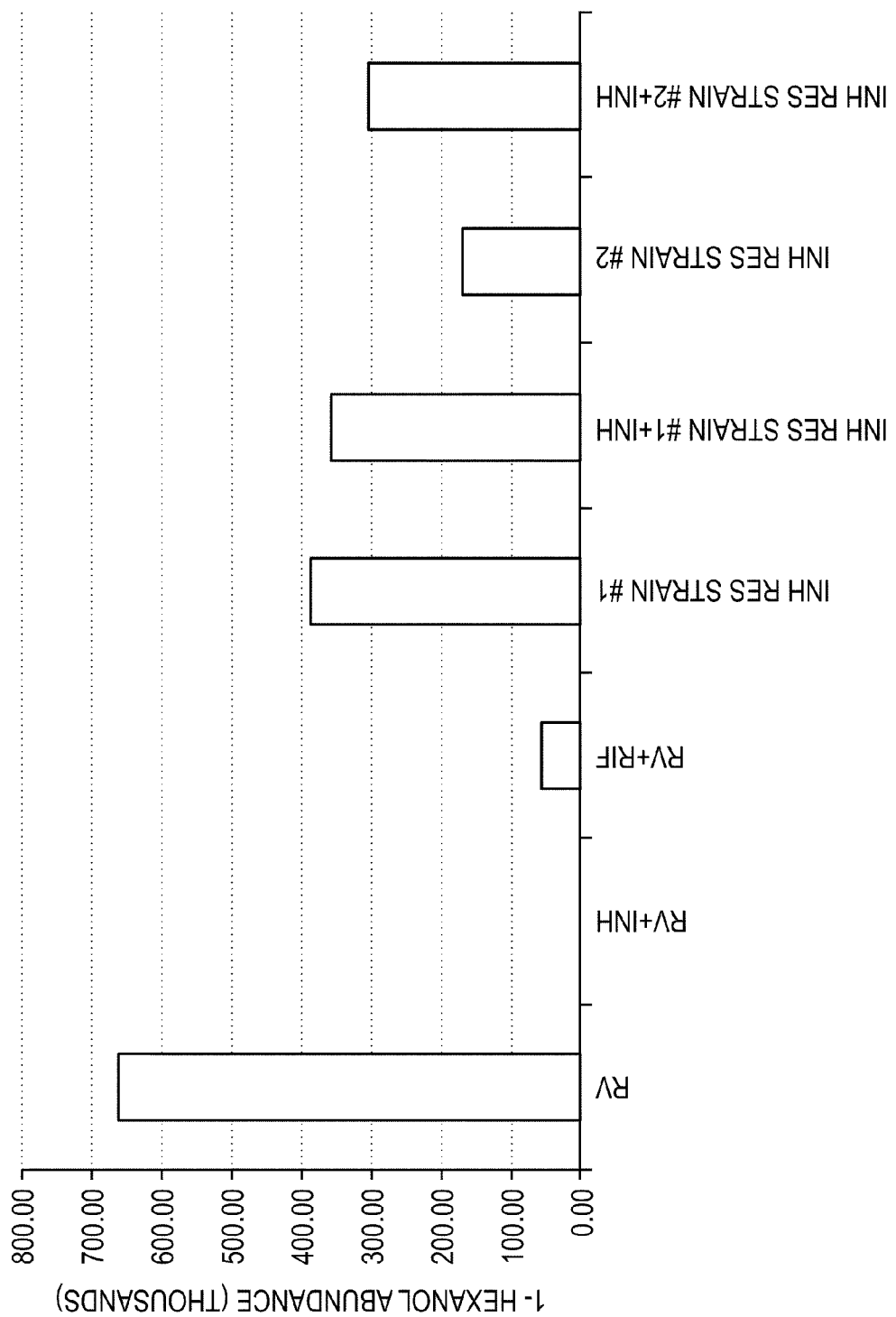
FIG. 18 is a graph showing the abundance of 1-hexanol in a sample from the headspace of cultures containing Mtb sensitive, Mtb singly resistant strain No. 1, Mtb singly resistant strain No. 2, Mtb sensitive strain exposed to INH, Mtb sensitive strain exposed to RIF, Mtb singly resistant strain No. 1 exposed to INH, or Mtb singly resistant strain No. 2 exposed to INH, as explained in Example 8.

Results:

Analytical analysis identified the presence of the VOCs methyl propionate, ethyl propionate, 1-pentanol, methyl pentanoate, 1-hexanol, ethyl pentanoate, methyl hexanoate, and ethyl hexanoate from the headspace of Mtb RV laboratory strain culture. Analytical analysis of a sample from the headspace of a *Escherichia coli* culture did not identify methyl propionate, methyl hexanoate, or ethyl hexanoate. Analytical analysis of samples from the headspace of *Mycobacterium smegmatis* and *Mycobacterium fortuitum* cultures lead to identification of the VOCs methyl propionate, ethyl propionate, 1-pentanol, methyl pentanoate, 1-hexanol, ethyl pentanoate, methyl hexanoate, and ethyl hexanoate. The concentration of the VOCs from the headspace of the cultures from *Mycobacterium smegmatis* and *Mycobacterium fortuitum* is sufficiently different from the concentration of the VOCs from the headspace of the Mtb RV laboratory strain culture to permit identification of the Mtb RV laboratory strain. FIG. 13 is a chart showing the peak area for the identified VOCs compounds in the GC-MS total ion chromatograph of the samples isolated from the headspace of the bacteria cultures.

Example 5

Identification of Volatile Organic Compounds in a Headspace Sample Following Incubation of *Mycobacterium Tuberculosis* at Different Temperatures and for Different Periods of Time Part I: Incubation of *Mycobacterium Tuberculosis* at Different Temperatures General Experimental Procedure:

In a first bacterial culture, *Mycobacterium tuberculosis* RV laboratory strain was incubated at 37° C. for 24 hours in minimal media containing sodium propionate, cholesterol, sodium pentanoate, and sodium hexanoate. In a second bacterial culture, *Mycobacterium tuberculosis* RV laboratory strain was incubated at 27° C. for 24 hours in minimal media containing sodium propionate, cholesterol, sodium pentanoate, and sodium hexanoate. After incubation for the specified time period, volatile organic compounds (VOCs) from each culture were extracted from the headspace and analyzed according to the general experimental procedures described in Example 2.

Results:

Analytical analysis identified the presence of the VOCs methyl pentanoate, 1-hexanol, and methyl hexanoate from the headspace of the culture performed at 37° C. and the culture performed at 27° C. FIG. 14 is an overlay of i) a GC-MS total ion chromatograph of a sample isolated from the headspace of a Mtb RV culture performed at 37° C., ii) a GC-MS total ion chromatograph of a sample isolated from the headspace of a Mtb RV culture performed at 27° C., and iii) a GC-MS total ion chromatograph of a sample isolated from the headspace of a culture containing just media.

Part II: Incubation of *Mycobacterium Tuberculosis* for Different Periods of Time General Experimental Procedure:

Mtb RV laboratory strain bacteria at a concentration of $10^8$ bacilli/mL were incubated in minimal media containing sodium propionate, cholesterol, sodium pentanoate, and sodium hexanoate for a period of 3 hours, 6 hours, 8 hours, and 12 hours. After the bacteria incubated for the indicated time period, volatile organic compounds (VOCs) were extracted from the headspace and analyzed according to the general experimental procedures described in Example 2.

Results:

Analytical analysis identified the presence of the VOCs methyl pentanoate, 1-hexanol, and methyl hexanoate from the headspace of the culture after incubation for 3 hours. FIG. 15 is an overlay of i) a GC-MS total ion chromatograph of a sample isolated from the headspace of a Mtb RV culture after incubation for 3 hours, ii) a GC-MS total ion chromatograph of a sample isolated from the headspace of a culture containing just media after incubation for 3 hours, and iii) a GC-MS total ion chromatograph of a sample isolated from the headspace of a Mtb RV culture after incubation for 24 hours.

Example 6

Identification of Volatile Organic Compound Biomarkers in Sputum Spiked with *Mycobacterium Tuberculosis*

General Experimental Procedure:

Sputum was harvested from patients that either i) have suspected TB and were sputum smear negative, or ii) have been undergoing treatment for TB for greater than 1 month and are sputum negative. Fresh sputum was collected and shipped overnight on ice (or frozen at −20° C.) for use in this experiment. Then, a 400 μL aliquot of sputum was re-suspended without addition of a homogenization solution (such as N-acetyl cysteine) in media containing sodium propionate and cholesterol to a final volume of approximately 1 mL. The sputum/media solution was then spiked with $10^6$ Mtb bacilli. After incubation for 24 hours, volatile organic compounds (VOCs) were extracted from the headspace of the culture and analyzed according to the general experimental procedures described in Example 2.

Results:

Analytical analysis by DMS identified the presence of methyl propionate from the headspace of cultures (i.e., cultures containing media, frozen sputum, or fresh sputum) spiked with Mtb. By comparison, analytical analysis by DMS did not identify methyl propionate from the headspace of cultures (i.e., cultures containing media, frozen sputum, or fresh sputum) that were not spiked with Mtb. FIG. 16 shows plots of DMS data obtained in Example 6. (FIG. 16 Top shows plots of DMS data obtained from a sample from the headspace of cultures (i.e., cultures containing frozen sputum, fresh sputum, or just media) that were not spiked with Mtb.

FIG. 16 Bottom shows plots of DMS data obtained from a sample from the headspace of cultures (i.e., cultures containing frozen sputum, fresh sputum, or just media) that were spiked with Mtb).

Example 7

Identification of Volatile Organic Compound Biomarkers in Sputum from Human Patients with *Mycobacterium Tuberculosis*

General Experimental Procedure:

Sputum was harvested from patients infected with *Mycobacterium tuberculosis*. Then, a 1 mL aliquot of sputum was admixed with media containing sodium propionate, sodium hexanoate, sodium pentanoate, and cholesterol to a final volume of approximately 2 mL. After incubation for 24 hours, volatile organic compounds (VOCs) were extracted from the headspace of the culture and analyzed according to the general experimental procedures described in Example 2.

Results:

Analytical analysis of a sample from the headspace of the culture identified multiple VOC biomarkers, and, of these, methyl hexanoate was the VOC biomarker having the highest concentration. FIG. 17 is a graph showing the abundance of methyl hexanoate in a sample from the headspace of the culture from patients with Mtb and a sample from the headspace of the culture of pooled sputum (i.e., negative sputum) from patients confirmed not to be infected with Mtb.

Example 8

Identification of Volatile Organic Compound Biomarkers from Mtb Exposed to an Antibiotic General Experimental Procedure:

Mtb sensitive (i.e., *Mycobacterium tuberculosis* RV laboratory strain) and singly resistant strains were incubated for 24 hours in the presence of isoniazid (INH) or rifampicin (RIF). The INH or RIF was present at a concentration corresponding to the LD90 (i.e., the dose at which 90% of the population of Mtb are expected to die) of INH or RIF, respectively. After this incubation period, media containing sodium propionate, sodium hexanoate, sodium pentanoate, and cholesterol were added to the Mtb culture and incubated for an additional 24 hours. After the incubation period, volatile organic compounds (VOCs) were extracted from the headspace of the culture and analyzed according to the general experimental procedures described in Example 2.

Results:

Analytical analysis of a sample from the headspace of the culture revealed that expression of several VOC biomarkers by sensitive Mtb was inhibited by drug treatment. In contrast, application of INH or RIF to drug resistant Mtb did not significantly effect expression of VOC biomarkers by the drug resistant Mtb. To illustrate, administration of a lethal dose 100 (LD100) of INH to sensitive strain Mtb inhibited the expression of 1-hexanol to such a degree that no 1-hexanol was identified by the analytical analysis. In contrast, the two INH resistant strains continued to express 1-hexanol even when these Mtb strains where exposed to INH. These results show that it is possible to distinguish sensitive Mtb strains from Mtb strains that are resistant to certain antibiotics by measuring the abundance of the volatile biomarkers produced in the presence and absence of antibiotic treatment. FIG. 18 is a graph showing the abundance of 1-hexanol in a sample from the headspace of the cultures from Mtb sensitive, Mtb singly resistant strain No. 1, Mtb singly resistant strain No. 2, Mtb sensitive exposed to INH, Mtb sensitive exposed to RIF, Mtb singly resistant strain No. 1 exposed to INH, and Mtb singly resistant strain No. 2 exposed to INH.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for identifying *Mycobacterium tuberculosis* bacteria in a sample, the method comprising:

detecting one or more volatile organic compounds associated with *Mycobacterium tuberculosis* metabolism, wherein the volatile organic compounds are indicative of at least one of a presence of, response to treatment of, and resistance of the *Mycobacterium tuberculosis* bacteria in the sample, the one or more volatile organic compounds being selected from the group consisting of ethyl propionate, 1-pentanol, methyl valerate, 1-hexanol, ethyl valerate, methyl caproate, ethyl caproate, and any of the foregoing compounds in isotopically labeled form;

determining the amount of the one or more volatile organic compounds; and identifying *Mycobacterium tuberculosis* in the sample based on presence and concentration of one or more volatile organic compounds.

2. The method of claim 1, wherein the one or more volatile organic compounds comprises methyl caproate.

3. The method of claim 1, wherein the one or more volatile organic compounds comprises 1-hexanol.

4. The method of claim 1, wherein a combination of two or more volatile organic compounds is indicative of the presence of or response to treatment or resistance of *Mycobacterium tuberculosis* in the sample.

5. The method of claim 1, wherein the one or more volatile organic compounds comprises methyl caproate and 1-hexanol.

6. The method of claim 1, further comprising collecting from a subject a sample suspected of comprising *Mycobacterium tuberculosis* bacteria.

7. The method of claim 1, further comprising detecting one or more volatile organic compounds associated with *Mycobacterium tuberculosis* metabolism indicating at least one of a presence of, response to treatment, and resistance of the *Mycobacterium tuberculosis* bacteria in the sample, the one or more volatile organic compounds being selected from the group consisting of methoxybenzene (anisole), methyl 2-ethylhexanoate, a chiral version of methyl 2-ethyl hexanoate, methyl propionate, 2-pentanone, 3-pentanone, 2,4-dimethyl-1-heptene, methyl isobutyl ketone, 6-methyl-5-hepten-2-one, dimethylsulfoxide, methyl 2-methylpropionate, 1-ethoxy-2-methylpropane, 1-ethoxybutane, t-butyl ethyl ether, isobutanol, and any of the foregoing compounds in isotopically labeled form.

8. The method of claim 7, wherein the method comprises detecting methyl caproate and methyl propionate.

9. The method of claim 1, wherein the sample was exposed to a candidate therapy for treating *Mycobacterium tuberculosis*.

10. The method of claim 1, wherein the sample comprises exhaled breath from an individual.

11. The method of claim 1, wherein the sample is selected from the group consisting of sputum, blood, urine, pleural fluid, gastric lavage, and pleural biopsy tissue.

12. The method of claim 1, wherein the detecting is performed using a portable device.

13. The method of claim 1, wherein the detecting is performed using a differential mobility spectrometer.

14. A method for identifying *Mycobacterium tuberculosis* bacteria in a sample, the method comprising:
    culturing a sample in a media comprising an alkali metal propionate, an alkali metal pentanoate, an alkali metal hexanoate, cholesterol, or any of the foregoing compounds in isotopically labeled form;
    detecting one or more volatile organic compounds associated with *Mycobacterium tuberculosis* metabolism indicating at least one of a presence of, response to treatment of, and resistance of the *Mycobacterium tuberculosis* bacteria from the cultured sample, the one or more volatile organic compounds being selected from the group consisting of ethyl propionate, 1-pentanol, methyl valerate, 1-hexanol, ethyl valerate, methyl caproate, ethyl caproate, and any of the foregoing compounds in isotopically labeled form;
    determining the amount of the one or more volatile organic compounds; and
    identifying *Mycobacterium tuberculosis* in the sample based on presence and concentration of one or more volatile organic compounds.

15. The method of claim 14, wherein the one or more volatile organic compounds comprises methyl caproate.

16. The method of claim 14, wherein the one or more volatile organic compounds comprises 1-hexanol.

17. The method of claim 14, wherein a combination of two or more volatile organic compounds is indicative of the presence of or response to treatment or resistance of *Mycobacterium tuberculosis* from the cultured sample.

18. The method of claim 14, wherein the sample is selected from the group consisting of sputum, blood, urine, pleural fluid, gastric lavage, and pleural biopsy tissue.

19. The method of claim 14, wherein the sample is sputum.

20. The method of claim 14, further comprising extracting the one or more volatile organic compounds from the culture by solid phase microextraction from a headspace of the culture or thermal desorption from a headspace of the culture to provide a more concentrated sample of the one or more volatile organic compounds for detection.

21. The method of claim 14, further comprising, prior to culturing the sample, collecting the sample from a subject.

* * * * *